United States Patent
Sakakibara et al.

(10) Patent No.: US 12,290,364 B2
(45) Date of Patent: May 6, 2025

(54) MENTAL AND PHYSICAL CONDITION ESTIMATION SYSTEM, MENTAL AND PHYSICAL CONDITION ESTIMATION METHOD, AND STORAGE MEDIUM

(71) Applicant: TOYOTA JIDOSHA KABUSHIKI KAISHA, Toyota (JP)

(72) Inventors: Kiyomi Sakakibara, Iwakura (JP); Hitoshi Yamada, Toyota (JP); Yuhei Yamaguchi, Toyota (JP); Chie Imamura, Nagoya (JP); Keiji Hayashi, Toyota (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 376 days.

(21) Appl. No.: 17/699,592

(22) Filed: Mar. 21, 2022

(65) Prior Publication Data
US 2022/0361790 A1    Nov. 17, 2022

(30) Foreign Application Priority Data

May 14, 2021    (JP) .................................. 2021-082700

(51) Int. Cl.
    *A61B 5/16*     (2006.01)
    *A61B 5/00*     (2006.01)
    *A61B 5/024*    (2006.01)
    *A61M 21/00*    (2006.01)

(52) U.S. Cl.
    CPC .......... *A61B 5/165* (2013.01); *A61B 5/02405* (2013.01); *A61B 5/4836* (2013.01); *A61B 5/7278* (2013.01); *A61M 21/00* (2013.01); *A61M 2021/0044* (2013.01)

(58) Field of Classification Search
    None
    See application file for complete search history.

(56) References Cited

U.S. PATENT DOCUMENTS

| | | | |
|---|---|---|---|
| 2014/0276090 A1* | 9/2014 | Breed | A61B 5/1455 600/473 |
| 2018/0133507 A1* | 5/2018 | Malchano | A61B 5/38 |
| 2019/0251858 A1 | 8/2019 | Baharav et al. | |
| 2021/0137452 A1 | 5/2021 | Mitsukura et al. | |
| 2022/0212029 A1* | 7/2022 | Lee | A61B 5/28 |

FOREIGN PATENT DOCUMENTS

| | | |
|---|---|---|
| CN | 105943015 A | 9/2016 |
| CN | 110916631 A | 3/2020 |
| JP | 2016-129629 A | 7/2016 |
| JP | 2016-162109 A | 9/2016 |
| JP | 2017-038759 A | 2/2017 |
| JP | 2018-088966 A | 6/2018 |
| JP | 2019-069207 A | 5/2019 |
| JP | 6727432 B2 | 7/2020 |

\* cited by examiner

*Primary Examiner* — William J Levicky
*Assistant Examiner* — Willow Grace Welch
(74) *Attorney, Agent, or Firm* — Oliff PLC

(57) ABSTRACT

A mental and physical condition estimation system according to the present disclosure includes: a heart rate information acquisition unit for acquiring heart rate information that is information related to a heart rate of a subject person; a heart rate variability calculation unit for calculating heart rate variability of a very low frequency component (VLF) from the acquired heart rate information; and a mental and physical condition estimation unit for estimating a concentration and effort state of the subject person from a calculated value of the heart rate variability.

6 Claims, 16 Drawing Sheets

FIG. 6

| CONTROL ITEM | CONTROL CONTENT | CONTROL EXAMPLE |
|---|---|---|
| HEARING | SOUND | SOUND OF LEAVES RUSTLING IN WIND |
| SMELL | SCENT | ROSEMARY ESSENTIAL OIL |
| TOUCH | SEAT VIBRATION | VIBRATION AT VLF CYCLE OF SUBJECT PERSON |
| VISION | COLOR TEMPERATURE, ILLUMINANCE BLINKING CYCLE | BLINK DISPLAY (BLUE) AT VLF CYCLE OF SUBJECT PERSON |

FIG. 7

| CONTROL ITEM | CONTROL CONTENT | CONTROL EXAMPLE |
|---|---|---|
| HEARING | SOUND | SOUND OF TRICKLING WATER BY BROOK |
| SMELL | SCENT | CYPRESS ESSENTIAL OIL |
| TOUCH | SEAT VIBRATION | VIBRATION AT HF CYCLE OF SUBJECT PERSON |
| VISION | COLOR TEMPERATURE, ILLUMINANCE BLINKING CYCLE | BLINK DISPLAY (BLUE) AT HF CYCLE OF SUBJECT PERSON |

FIG. 10

| CONTROL ITEM | CONTROL CONTENT | CONCENTRATED FOR LARGE VLF | ACTIVATED FOR LARGE LF/HF | INSPIRED AND RELAXED FOR LARGE HF |
|---|---|---|---|---|
| | | (e)→(a) (c)<br>(f)→(a) (c) | (c)→(a), (d)→(a)<br>(f)→(a) | (b)→(c) (d)<br>(e)→(c) (d) |
| TEMPERATURE | TEMPERATURE RANGE HIGH/LOW | MODERATE 24°C TO 26°C | MODERATE 24°C TO 26°C | HIGH 25°C TO 27°C |
| HEARING | SOUND | SOUND OF LEAVES RUSTLING IN WIND | BIRDS SINGING | SOUND OF TRICKLING WATER BY BROOK |
| SMELL | SCENT | ROSEMARY ESSENTIAL OIL | GRAPEFRUIT ESSENTIAL OIL | CYPRESS ESSENTIAL OIL |
| TOUCH | SEAT VIBRATION | VIBRATION AT VLF CYCLE OF SUBJECT PERSON | VIBRATION AT LF CYCLE OF SUBJECT PERSON | VIBRATION AT HF CYCLE OF SUBJECT PERSON |
| VISION (LIGHT) | COLOR TEMPERATURE, ILLUMINANCE BLINKING CYCLE | BLINK DISPLAY (BLUE) AT VLF CYCLE OF SUBJECT PERSON | BLINK DISPLAY (RED) AT LF CYCLE OF SUBJECT PERSON | BLINK DISPLAY (BLUE-GREEN) AT HF CYCLE OF SUBJECT PERSON |
| VISION (OTHER THAN LIGHT) | TYPE OF PLANTS | PLANTS WITH ELONGATED LEAVES OR IMAGE THEREOF | PLANTS WITH LARGE LEAVES OR IMAGE THEREOF | PLANTS WITH SMALL, ROUND LEAVES OR IMAGE THEREOF |
| WIND | FLUCTUATION CYCLE OF WIND SPEED AND FLUCTUATION FREQUENCY DISTRIBUTION | CHANGE WIND SPEED AT VLF CYCLE OF SUBJECT PERSON | CHANGE WIND SPEED AT LF CYCLE OF SUBJECT PERSON | CONTROL WIND SPEED TO ACHIEVE 1/f FLUCTUATION |

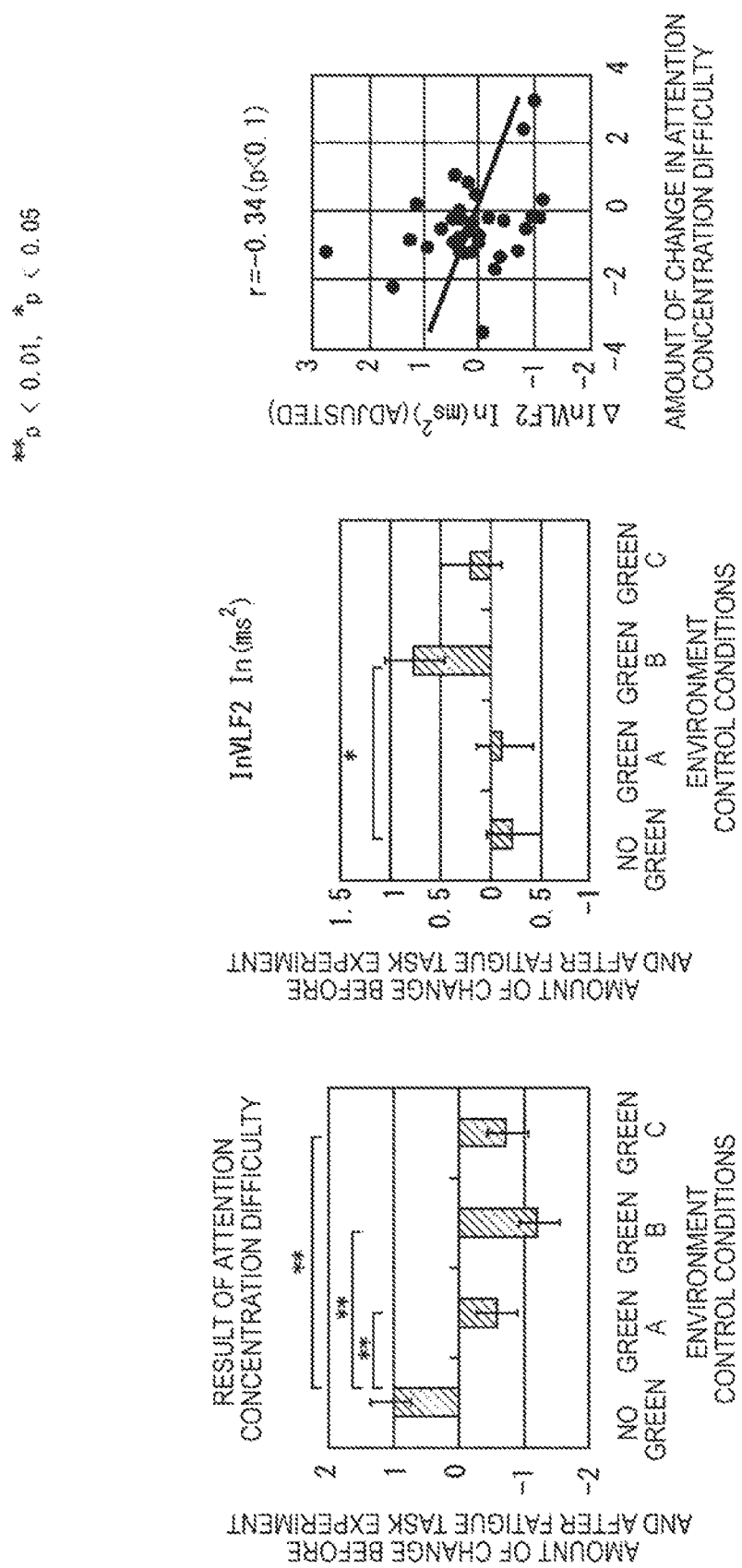

MENTAL AND PHYSICAL CONDITION ESTIMATION SYSTEM, MENTAL AND PHYSICAL CONDITION ESTIMATION METHOD, AND STORAGE MEDIUM

CROSS-REFERENCE TO RELATED APPLICATION

This application claims priority to Japanese Patent Application No. 2021-082700 filed on May 14, 2021, incorporated herein by reference in its entirety.

BACKGROUND

1. Technical Field

The present disclosure relates to a mental and physical condition estimation system, a mental and physical condition estimation method, and a storage medium.

2. Description of Related Art

Japanese Unexamined Patent Application Publication No. 2018-088966 (JP 2018-088966 A) discloses a technique related to a mental and physical condition (mood) estimation system using a heart rate and a sympathetic nerve activity index (LF/HF) of a subject person.

SUMMARY

The inventors have found that the mental and physical condition estimation system in the related art has room for improvement in estimation accuracy.

The present disclosure has been made in view of the above issue. The present disclosure estimates the mental and physical condition from the value of a very low frequency component (VLF) of the heart rate variability. The present disclosure provides a mental and physical condition estimation system, a mental and physical condition estimation method, and a storage medium capable of estimating the mental and physical condition of a subject person with higher accuracy.

A mental and physical condition estimation system according to the present disclosure includes: a heart rate information acquisition unit for acquiring heart rate information that is information related to a heart rate of a subject person; a heart rate variability calculation unit for calculating heart rate variability of a very low frequency component (VLF) from the acquired heart rate information; and a mental and physical condition estimation unit for estimating a concentration and effort state of the subject person from a calculated value of the heart rate variability.

The mental and physical condition estimation system according to the present disclosure can estimate the concentration and effort state of the subject person with higher accuracy.

Further, the heart rate variability calculation unit calculates the heart rate variability for each of VLF1 and VLF2 having a lower frequency band than the VLF1. Each of the VLF1 and the VLF2 is included in the VLF. The mental and physical condition estimation unit estimates the concentration and effort state of the subject person from a value of the VLF2, and estimates a fatigue state from a value of the VLF1.

In addition to estimating the concentration and effort state, the mental and physical condition estimation system according to the present disclosure can also estimate the fatigue state.

Further, the heart rate variability calculation unit further calculates the heart rate variability of a high frequency component (HF) and a low frequency component (LF). The mental and physical condition estimation unit estimates a fatigue state in addition to the concentration and effort state of the subject person from the VLF, the HF, and the LF.

In addition to estimating the concentration and effort state, the mental and physical condition estimation system according to the present disclosure can also estimate the fatigue state.

The mental and physical condition estimation system further includes an environment control unit for controlling an environment of the subject person based on an estimated mental and physical condition.

The mental and physical condition estimation system according to the present disclosure can achieve an optimal mental and physical state for the subject person by controlling the environment around the subject person.

The environment control unit performs control to increase concentration when the concentration and effort state estimated by the mental and physical condition estimation unit is equal to or lower than a predetermined level.

The mental and physical condition estimation system according to the present disclosure can increase the concentration when the concentration of the subject person is reduced.

The mental and physical condition estimation system further includes an environment control unit for controlling an environment of the subject person based on an estimated mental and physical condition. The environment control unit performs control to alleviate fatigue when the fatigue state estimated by the mental and physical condition estimation unit is equal to or higher than a predetermined level.

The mental and physical condition estimation system according to the present disclosure can alleviate fatigue when the subject person is fatigued.

The mental and physical condition estimation system further includes a target setting unit for setting a target of the mental and physical condition. The environment control unit controls the environment around the subject person based on the estimated mental and physical condition and the set target of the mental and physical condition.

The mental and physical condition estimation system according to the present disclosure can adjust the mental and physical condition of the subject person to a desired mental and physical condition as a target with the target setting unit.

The target setting unit sets the target based on a predetermined schedule.

The mental and physical condition estimation system according to the present disclosure can automatically set a target based on the schedule of the subject person even when the subject person does not set the target by himself/herself.

A mental and physical condition estimation method according to the present disclosure includes: a step of acquiring heart rate information that is information related to a heart rate of a subject person; a step of calculating a heart rate variability of a very low frequency component (VLF) from the acquired heart rate information; and a step of estimating a concentration and effort state of the subject person from a calculated value of the heart rate variability.

The mental and physical condition estimation method according to the present disclosure can estimate the concentration and effort state of the subject person with higher accuracy.

A storage medium according to the present disclosure stores a mental and physical condition estimation program. The mental and physical condition estimation program causes a computer to execute: a step of acquiring heart rate information that is information related to a heart rate of a subject person; a step of calculating a heart rate variability of a very low frequency component (VLF) from the acquired heart rate information; and a step of estimating a concentration and effort state of the subject person from a calculated value of the heart rate variability.

The mental and physical condition estimation program stored in the storage medium according to the present disclosure can estimate the concentration and effort state of the subject person with higher accuracy.

The present disclosure can provide a mental and physical condition estimation system, a mental and physical condition estimation method, and a storage medium capable of estimating the mental and physical condition from the value of the very low frequency component (VLF) of the heart rate variability and estimating the mental and physical condition of the subject person with higher accuracy.

BRIEF DESCRIPTION OF THE DRAWINGS

Features, advantages, and technical and industrial significance of exemplary embodiments of the disclosure will be described below with reference to the accompanying drawings, in which like signs denote like elements, and wherein:

FIG. 6 is a table showing an example of environment control performed by an environment control unit 14 of the mental and physical condition estimation system according to the second embodiment;

FIG. 7 is a table showing an example of the environment control performed by the environment control unit of the mental and physical condition estimation system according to the second embodiment;

FIG. 10 is a table showing an example of environment control performed by an environment control unit of the mental and physical condition estimation system according to the third embodiment;

FIG. 16 are graphs showing results of comparison of the average value of VLF2 for the subjective evaluation "attention concentration difficulty" according to a fourth example and a correlation analysis thereof.

DETAILED DESCRIPTION OF EMBODIMENTS

First Embodiment

A mental and physical condition estimation system according to the present embodiment is a system for calculating a heart rate variability of a very low frequency component (VLF) based on heart rate information that is information related to a heart rate of a subject person, and estimating a mental and physical condition of the subject person. In this specification, the calculated VLF is described as "VLP" or "VLF signal". Hereinafter, the mental and physical condition estimation system according to the present embodiment will be described in detail with reference to FIGS. 1 to 3.

Figure 1:
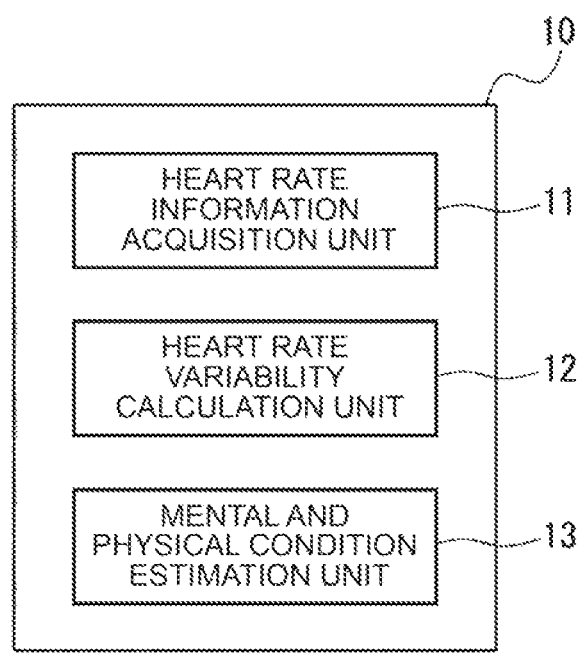
FIG. 1 is a block diagram showing a mental and physical condition estimation system according to a first embodiment.

FIG. 1 is a block diagram showing a mental and physical condition estimation system according to a first embodiment. As shown in FIG. 1, a mental and physical condition estimation system 10 includes a heart rate information acquisition unit 11, a heart rate variability calculation unit 12, and a mental and physical condition estimation unit 13.

1. Heart Rate Information Acquisition Unit

The heart rate information acquisition unit 11 shown in FIG. 1 acquires the heart rate information that is information related to the heart rate of the subject person. The heart rate information acquisition unit 11 is, for example, an electrocardiograph (electrocardiograph sensor), a heart rate meter (optical transmission type pulse wave sensor, optical reflection type pulse wave sensor), a sphygmomanometer, a pressure sensor (piezoelectric element), a non-contact type sensor using a face image, a wearable device such as a commercially available smartwatch, or the like. The heart rate information acquisition unit 11 may be used by being embedded in a seat of a chair or a vehicle. The heart rate information is, for example, an electrocardiogram acquired by an electrocardiograph, but is not limited thereto. For example, information corresponding to an electrocardiogram can be acquired as the heart rate information from a pulse wave, an arterial pressure, or the like.

2. Heart Rate Variability Calculation Unit

The heart rate variability calculation unit 12 shown in FIG. 1 performs frequency analysis on the heart rate information of the subject person acquired by the heart rate information acquisition unit 11, and calculates values of the heart rate variability (HRV) for respective components in a particular frequency band. The term "heart rate variability"

in the present embodiment includes, for example, heart rate variation, pulse variation, and blood pressure beat interval variation.

As an example, the calculation of the heart rate variability performed by the heart rate variability calculation unit 12 will be described in the case where an electrocardiograph is used as the heart rate information acquisition unit 11 and an electrocardiogram is acquired as the heart rate information. The highest peak of the electrocardiogram acquired by the heart rate information acquisition unit 11 is called an R wave. In the electrocardiogram, the heart rate interval is indicated by an RR interval (RRI) that is the interval between an R wave and an R wave. The heart rate variability refers to the periodic fluctuations that occur in the RR interval.

The heart rate variability calculation unit 12 calculates time series data of the heart rate variability obtained by calculating the RR interval from the electrocardiogram. When frequency analysis is performed on the time series data of the heart rate variability, a graph of power spectral density (PSD) is obtained in which the horizontal axis represents frequency (Hz) and the vertical axis represents power ($msec^2$/Hz). A known analysis method can be used for the frequency analysis. Specifically, for example, a Fast Fourier Transform (FFT) method, a Maximum Entropy (MEM)method, or the like may be used.

The obtained graph of the power spectral density has a particular peak at a particular frequency band. The heart rate variability calculation unit 12 calculates (1) the value of the very low frequency component (VLF) as the value of the heart rate variability for each frequency band. Instead of (1), (2) the values of the VLF1 and the VLF2 included in the VLF may be calculated. Alternatively. (3) the values of the VLF, the low frequency (F) component, and the high frequency (HF) component may be calculated. Details of the calculation of each value of the heart rate variability will be described later.

In the present embodiment, the value of the VLF can be used as an index indicating the function of the sympathetic nerve. In particular, the value of the VLF can be used to estimate the concentration and effort state, the value of the VLF1 can be used to estimate the fatigue state, and the value of the VLF2 can be used to estimate the concentration and effort state. Here, the "effort state" refers to a state in which the subject person makes an effort using his/her mind or body to achieve a goal. The value of the LF is known as an index indicating the sympathetic nerve function of the subject person, the value of the HF is known as an index indicating the parasympathetic nerve function of the subject person, and the value of the LF/HF is known as an index indicating the sympathetic nerve function of the subject person.

The heart rate variability calculation unit 12 calculates in advance a normal value (threshold value) of the value of the heart rate variability of the subject person in the resting state in order to estimate the mental and physical condition of the subject person using the mental and physical condition estimation unit 13 described later. The normal value (threshold value) of the value of the heart rate variability is a value having a predetermined width. In order to calculate the normal value (threshold value) of the value of the heart rate variability, the heart rate variability calculation unit 12 acquires the heart rate information at least twice. The heart rate variability calculation unit 12 calculates the value of the heart rate variability from the acquired heart rate information. The standard deviation a may be obtained by calculating the average value of the values of the heart rate variability to set the range of ±2σ as the normal value (threshold value) of the value of the heart rate variability of the subject person.

When the normal value (threshold value) of the value of the heart rate variation of the subject person is not calculated in advance, the normal value (threshold value) may be calculated by using two or more pieces of the heart rate information or two or more values of the heart rate variability of another person acquired in advance. "Another person" means any person other than the subject person. The heart rate information or the value of the heart rate variability of the other person may be a value acquired twice or more from one person different from the subject person. The heart rate information or the value of the heart rate variability of the other person may be a value acquired one or more times each from a plurality of persons different from the subject person. The standard deviation a may be obtained by calculating the average value of the values of the heart rate variability to set the range of ±2σ as the normal value (threshold value) of the value of the heart rate variability.

Hereinafter, the calculation of the value of the heart rate variability in the above (1) to (3) will be described in more detail.

(1) Value of VLF

The frequency band of the VLF may be a value equal to or lower than a frequency that can be transmitted by the sympathetic nerve. Specifically, the frequency band of the VLF is, for example, 0.0001 Hz to 0.05 Hz, and is preferably 0.0033 Hz to 0.04 Hz. However, the frequency band of the VLF is not limited thereto and may be defined by other frequency bands.

The value of the VLF may be calculated as an integral value (area) of the power in the frequency band of the VLF. Alternatively, the calculated integral value (area) of the power may be further divided by the width of the frequency band indicating the VLF to calculate the value of the VLF. The width of the frequency band of the VLF is obtained by subtracting the lower limit value from the upper limit value of the frequency band of the VLF.

(2) Values of VLF1 and VLF2 included in VLF

Further, the value of the VLF in (1) described above may be calculated as the more finely classified VLF1 component and VLF2 component. Both the VLF1 and the VLF2 are frequency bands included in the VLF in (1). The frequency band of the VLF1 is a frequency band higher than the frequency band of the VLF2. In other words, the frequency band of the VLF2 is a lower frequency band than the frequency band of the VLF1.

The relation between the VLF1 and the VLF2 will be described in detail. For example, the VLF1 and the VLF2 may be set so that a value of a given frequency is used as a border value to divide a frequency band into two frequency bands. Further, the VLF1 and the VLF2 may be set so that a part of the lower frequency band included in the VLF1 and a part of the higher frequency band included in the VLF2 overlap each other. Alternatively, the VLF1 and the VLF2 may be set so that the lower limit value of the frequency of the VLF1 and the upper limit value of the frequency of the VLF2 does not overlap and are spaced apart from each other.

When the VLF1 and the VLF2 are set so as to be divided into two frequency bands using a value of a given frequency as a boundary value, 0.015 Hz may be used as the boundary value as an example. This value is a value of ¹⁄₁₀ of 0.15 Hz, which is often used as a boundary value between LF and HF.

The values of the VLF1 and the VLF2 can be obtained by the same calculation method as that of the VLF in (1) described above. That is, the values of the VLF1 and the VLF2 may be calculated as integral values (areas) of the power in the respective frequency bands. Alternatively, the values of the VLF1 and the VLF2 may be obtained by further dividing the calculated integral value (area) of the power by the width of the frequency band indicating the VLF1 or the VLF2. The width of the frequency band of the VLF1 and the VLF2 is obtained by subtracting the lower limit value from the upper limit value of the respective frequency bands.

(3) Values of VLF, LF, and HF in addition to (1) or (2) described above, the values of the LF and the HF may be further calculated. The VLF may be any of the VLF in (1) and the VLF1 and the VLF2 in (2) described above. The frequency band of the LF may be a value that can be transmitted by the sympathetic nerve and the parasympathetic nerve. Specifically, the frequency band of the LF is 0.03 Hz to 0.20 Hz, and is preferably 0.04 Hz to 0.15 Hz, but is not limited thereto. The frequency band of the HF may be a value equal to or higher than the frequency that can be transmitted by the parasympathetic nerve. Specifically, the frequency band of the HF is 0.10 Hz to 0.5 Hz, and is preferably 0.15 Hz to 0.4 Hz. However, the frequency band of the HF is not limited thereto and may be defined by other frequency bands.

The values of the VLF or the VLF1 and the VLF2, the LF, and the HF can be obtained by the same calculation method as that of the VLF in (1) above. That is, each value may be calculated as an integral value (area) of the power in each frequency band. Alternatively, the value may be obtained by further dividing the calculated integral value (area) of the power by the width of the frequency band indicating each frequency band. The width of the frequency band is obtained by subtracting the lower limit value from the upper limit value of the respective frequency bands. In addition, the heart rate variability calculation unit 12 calculates an "LF/HF value" that is an index indicating the nervous state and fatigue from the value of the LF and the value of the HF. The LF/HF value is a value calculated by dividing the LF value by the HF value. Alternatively, an "ln(LF/HF) value" that is a logarithm of the LF/HF value may be used.

Although specific examples of the heart rate information and the heart rate variability have been described above, the heart rate information acquired by the heart rate information acquisition unit 11 is not limited to the specific example described above as long as the heart rate information is information related to at least the heart rate capable of calculating the VLF when the heart rate variability calculation unit 12 performs the frequency analysis.

For example, as another example of the heart rate information and the heart rate variability, a pulse may be acquired as the heart rate information by using a pulse wave meter as the heart rate information acquisition unit 11. The pulse has a periodicity associated with the heart rate. The heart rate variability calculated by the heart rate variability calculation unit 12 includes a periodic fluctuation occurring in a pulse interval (PI), that is, the pulse variation. Although the waveform of the pulse wave has a gradual peak as compared with the electrocardiogram, pulse interval information with higher accuracy may be acquired by obtaining an acceleration pulse wave that is a secondary differential wave from the acquired pulse wave waveform.

Alternatively, for example, a sphygmomanometer may be used as the heart rate information acquisition unit 11, and the beat interval may be acquired as the heart rate information. The heart rate variability calculated by the heart rate variability calculation unit 12 includes a beat interval variation. Specifically, the heart rate variability calculation unit 12 obtains a time series waveform of the beat interval acquired as the heart rate information, and performs frequency analysis on the time series waveform, thereby obtaining the beat interval variation.

3. Mental and Physical Condition Estimation Unit

The mental and physical condition estimation unit 13 shown in FIG. 1 estimates the mental and physical condition of the subject person from the value of the heart rate variability calculated by the heart rate variability calculation unit 12. The mental and physical condition of the subject person in the present embodiment specifically includes a concentration and effort state and a fatigue state. The subject person is a person who stays in a space closed to some extent and in which the environment around the subject person can be controlled, and is, for example, a driver of a vehicle, a pilot of an airplane, a person who works in a space such as an office or a shop, or a person who studies in a space such as a classroom or a room.

Each of the following describes cases in which the heart rate variability calculation unit 12 calculates (1) the value of the VLF, (2) the values of the VLF1 and the VLF2 included in the VLF, and (3) the values of the VLF, the LF, and the HF (LF/HF), as the value of the heart rate variability.

(1) When Calculating Value of VLF

When the value of the VLF calculated by the heart rate variability calculation unit 12 is smaller than the normal value (threshold value), the mental and physical condition estimation unit 13 estimates that the subject person is not concentrated compared to the resting state. On the contrary, when the value of the VLF is larger than the normal value (threshold value), the mental and physical condition estimation unit 13 estimates that the subject person is in the concentration and effort state compared to the resting state.

(2) When Calculating Values of VLF1 and VLF2 Included in VLF

Figure 2:
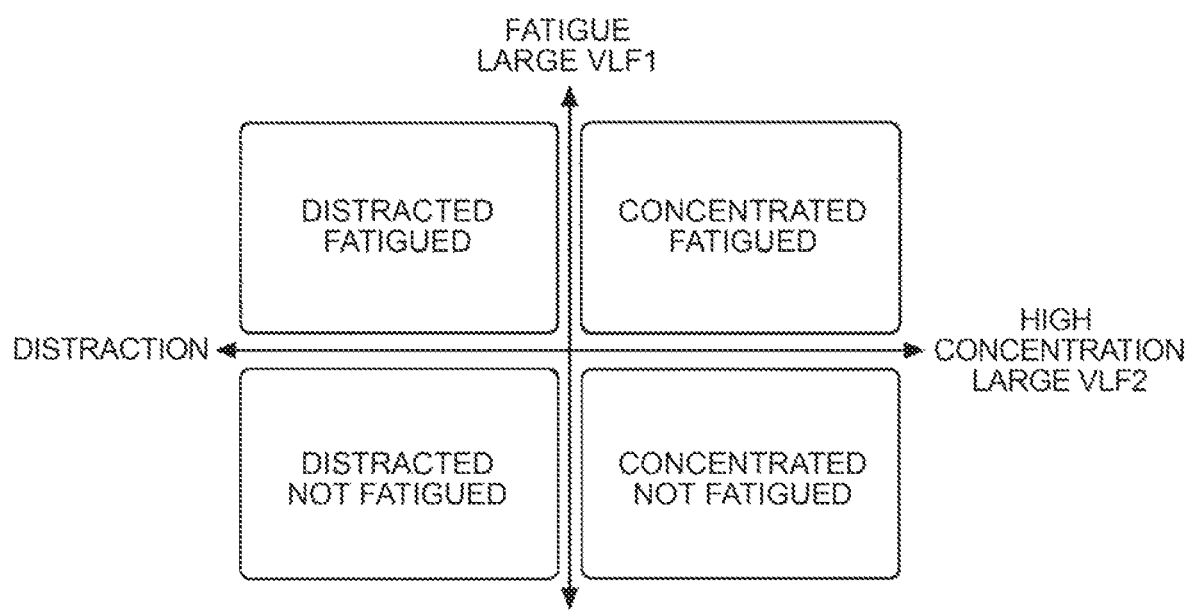
FIG. 2 is a diagram showing a relationship between VLF1 and a fatigue state and a relationship between VLF2 and a concentration state according to the first embodiment.

Description will be made with reference to FIG. 2. FIG. 2 is a diagram showing the relationship between the VLF1 and the fatigue state, and the relationship between the VLF2 and the concentration and effort state according to the first embodiment. As shown in FIG. 2, the VLF1 in the present embodiment indicates the fatigue state, and the VLF2 indicates the concentration and effort state. That is, when the values of the VLF1 and the VLF2 are calculated, in addition to estimating the concentration and effort state from the value of the VLF2, the fatigue state can also be estimated from the value of the VLF1.

When the value of the VLF1 calculated by the heart rate variability calculation unit 12 is larger than the normal value (threshold value), the mental and physical condition estimation unit 13 estimates that the subject person is fatigued more than in the resting state. On the contrary, when the value of the VLF1 is smaller than the normal value (threshold value), the mental and physical condition estimation unit 13 estimates that the subject person is not fatigued compared to the resting state.

When the value of the VLF2 calculated by the heart rate variability calculation unit 12 is larger than the normal value (threshold value), the mental and physical condition estimation unit 13 estimates that the subject person is more concentrated and effortful than in the resting state. On the contrary, when the value of the VLF2 is smaller than the normal value (threshold value), the mental and physical condition estimation unit 13 estimates that the subject person is not concentrated and is distracted compared to the resting state.

Further, estimation of the mental and physical condition when the values of the VLF1 and the VLF2 are combined will be described.

When the values of the VLF1 and the VLF2 calculated by the heart rate variability calculation unit 12 are larger than the normal values (threshold values), the mental and physical condition estimation unit 13 estimates that the subject person is more concentrated and effortful and is also more fatigued than in the resting state.

When the value of the VLF1 calculated by the heart rate variability calculation unit 12 is larger than the normal value (threshold value) and the value of the VLF2 is smaller than the normal value (threshold value), the mental and physical condition estimation unit 13 estimates that the subject person is not concentrated and is distracted and is also fatigued compared to the resting state.

When the value of the VLF1 calculated by the heart rate variability calculation unit 12 is smaller than the normal value (threshold value) and the value of the VLF2 is larger than the normal value (threshold value), the mental and physical condition estimation unit 13 estimates that the subject person is concentrated and effortful and is not fatigued.

When the values of the VLF1 and the VLF2 calculated by the heart rate variability calculation unit 12 are smaller than the normal values (threshold values), the mental and physical condition estimation unit 13 estimates that the subject person is not concentrated and is distracted, and is not fatigued.

(3) When Calculating Values of VLF, LF, and HF (LF/HF)

Figure 3:
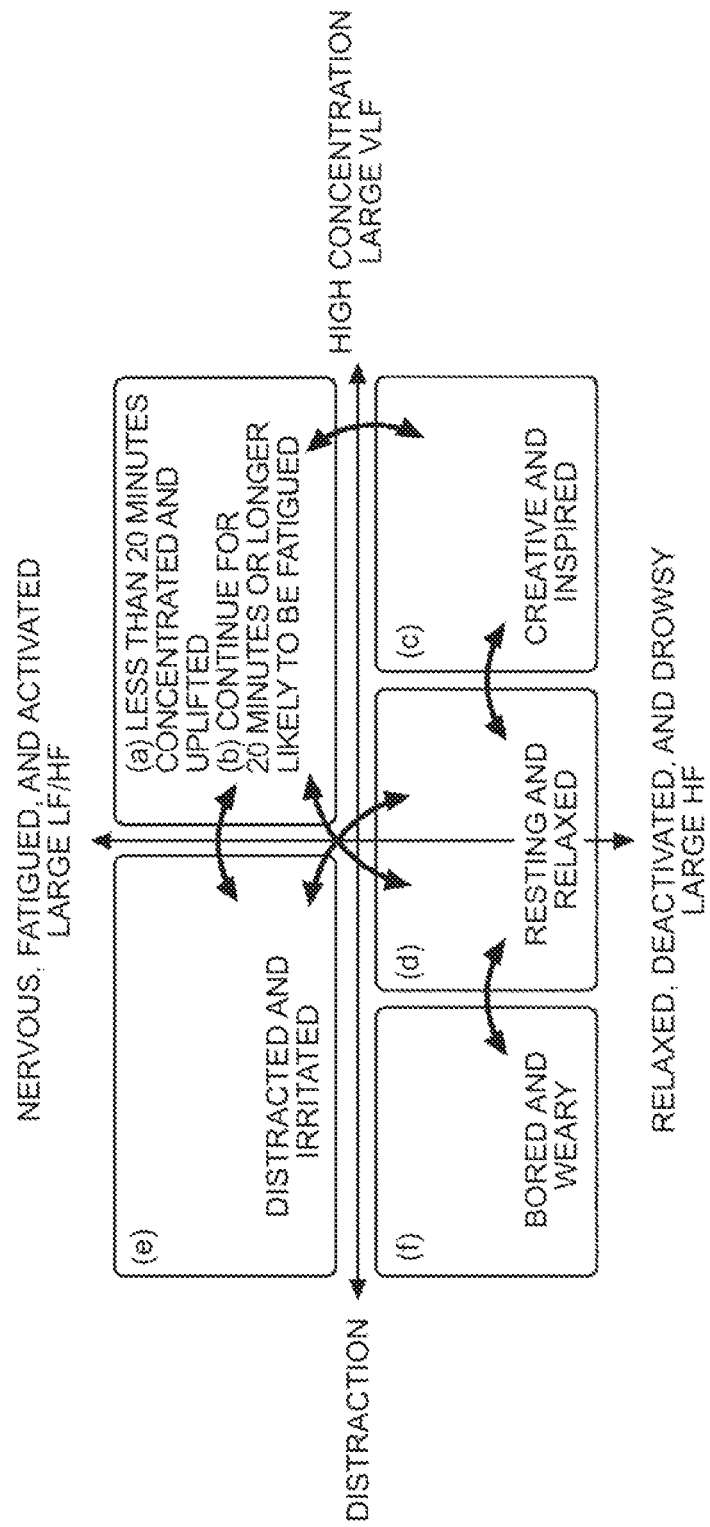
FIG. 3 is a diagram showing a classification of a mental and physical condition based on a value of a heart rate variability according to the first embodiment.

Description will be made with reference to FIG. 3. FIG. 3 is a diagram showing the classification of the mental and physical condition based on the value of the heart rate variability according to the first embodiment. As described above in (1), the VLF indicates the concentration and effort state. When the values of the LF and the HF are calculated in addition to the VLF, the mental and physical condition estimation unit 13 estimates the fatigue state in addition to the concentration and effort state.

Estimation of the mental and physical condition when the values of the VLF, the HF, and the LF/HF are combined will be described below by dividing states into (a) to (f). The following description of (a) to (f) corresponds to (a) to (f) in FIG. 3.

(a) Concentration State and Uplifting State: Large VLF, Large LF/HF, Less than 20 Minutes When the value of the VLF calculated by the heart rate variability calculation unit 12 is larger than the normal value (threshold value) and the value of the LF/HF is larger than the normal value (threshold value), and the state indicating the values lasts continuously or intermittently for less than 20 minutes in total, the mental and physical condition estimation unit 13 estimates that the subject person is in a concentration and effort state and an uplifted state.

(b) Fatigue State: Large VLF, Large LF/HF, 20 Minutes or More

On the other hand, when the value of the VLF calculated by the heart rate variability calculation unit 12 is larger than the normal value (threshold value) and the value of the LF/HF is larger than the normal value (threshold value) as in (a), but the state indicating the values lasts continuously or intermittently for 20 minutes or more in total, the mental and physical condition estimation unit 13 estimates that the subject person is likely to be fatigued.

(c) Creative and Inspired State: Large VLF, Large HF

When the value of the VLF calculated by the heart rate variability calculation unit 12 is larger than the normal value (threshold value) and the value of the HF is larger than the normal value (threshold value), the mental and physical condition estimation unit 13 estimates that the subject person is in a state suitable for performing a creative work or being inspired.

(d) Resting and Relaxed State: VLF within Range of Normal Value (Threshold Value), Large HF When the value of the VLF calculated by the heart rate variability calculation unit 12 is within the range of the normal value (threshold value) and the value of the HF is larger than the normal value (threshold value), the mental and physical condition estimation unit 13 estimates that the subject person is in a resting and relaxed state.

(e) Distracted and Irritated State: Small VLF, Large LF/HF

When the value of the VLF calculated by the heart rate variability calculation unit 12 is smaller than the normal value (threshold value) and the value of the LF/HF is larger than the normal value (threshold value), the mental and physical condition estimation unit 13 estimates that the subject person is in a distracted state with reduced concentration and is irritated.

(f) Bored and Weary State: Small VLF, Large HF

When the value of the VLF calculated by the heart rate variability calculation unit 12 is smaller than the normal value (threshold value) and the value of the HF is larger than the normal value (threshold value), the mental and physical condition estimation unit 13 estimates that the subject person is in a bored and weary state.

Note that the VLF may be classified more finely to the VLF1 and the VLF2 as described in (2) above. By checking both the fatigue state indicated by the value of the VLF1 and the nervousness and fatigue state indicated by the value of the LF/HF, the fatigue state can be estimated with higher accuracy.

Next, the mental and physical condition estimation method according to the present embodiment will be described.

Figure 4:
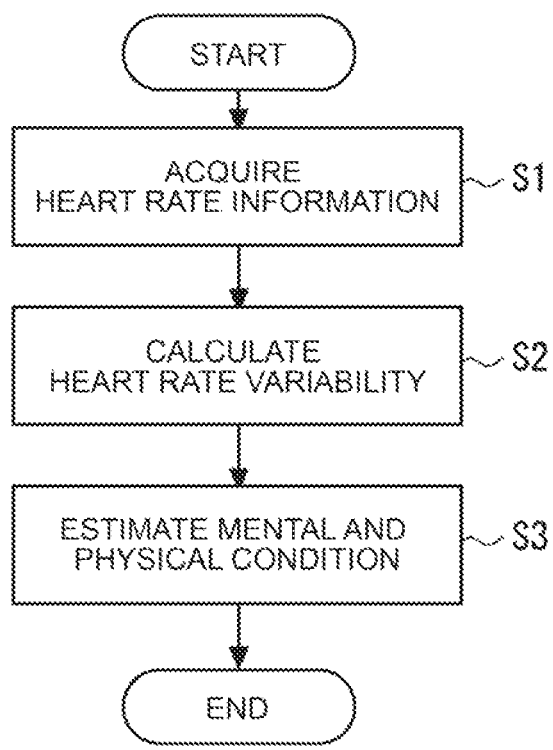
FIG. 4 is a flowchart showing a mental and physical condition estimation method according to the first embodiment.

FIG. 4 is a flowchart showing a mental and physical condition estimation method according to the first embodiment. As shown in FIGS. 1 and 4, the mental and physical condition estimation method according to the present embodiment includes a step (step S1) in which the heart rate information acquisition unit 11 acquires the heart rate information, a step (step S2) in which the heart rate variability calculation unit 12 calculates the heart rate variability, and a step (step S3) in which the mental and physical condition estimation unit 13 estimates the mental and physical condition.

The mental and physical condition estimation system and the mental and physical condition estimation method according to the present embodiment use the value of the VLF as an index of the concentration and effort state. A psychomotor vigilance test (PVT) is known as an example of a test capable of estimating a fatigued state or a hypoarousal state other than using the heart rate variability. Also known as a mental workload task is the n-back task.

The correlation between the performance in the PVT and the fatigue state estimated using the value of the VLF in the present embodiment is higher than the correlation between the performance in the PVT and the fatigue state estimated using the value of the LF/HF that is conventionally known as an index of mental fatigue. In addition, it is shown in the examples described later that although there is a correlation between the performance in the n-back task and the concentration and effort state estimated using the value of the VLF, no correlation is found between the performance in the n-back task and the LF/AI.

Further, it is shown in the examples described later that the VLF1 has a positive correlation with the performance in the PVT and the VLF1 increases in the fatigue state. In addition, it is shown in the examples described later that although no correlation is found between the VLF1 and the performance in the n-back task, the VLF2 has a negative correlation with the performance in the n-back task and the VLF2 increases in the concentration and effort state. Further, the VLF2 has a higher negative correlation with the performance in the n-back task than the VLF does.

Therefore, the mental and physical condition estimation system and the mental and physical condition estimation method according to the present embodiment estimate the concentration and effort state from the VLF that is the value of the heart rate variability having a higher correlation with the concentration and effort state as compared with the LF/HF, making it possible to estimate the concentration and effort state of the subject person with higher accuracy. Furthermore, by using the VLF1 correlated with the fatigue state and the VLF2 correlated with the concentration and effort state, the fatigue state and the concentration and effort state can be estimated simultaneously. In addition, by using the VLF2 having a higher negative correlation with the performance in the n-back task than the VLF does, it is possible to estimate the concentration and effort state with higher accuracy.

The correlation between the performance in the PVT and the performance in the n-back task and the VLF, the VLF1, the VLF2, and the LF/HF will be described later with reference to examples of specific correlation analytical results.

Second Embodiment

The mental and physical condition estimation system according to the present embodiment further includes an environment control unit that controls the environment of the subject person based on the mental and physical condition estimated by the mental and physical condition estimation system according to the first embodiment. The environment of the subject person is an environment of a space in which the subject person stays. Hereinafter, the mental and physical condition estimation system according to the present embodiment will be described with reference to FIGS. 5 and 6.

Figure 5:
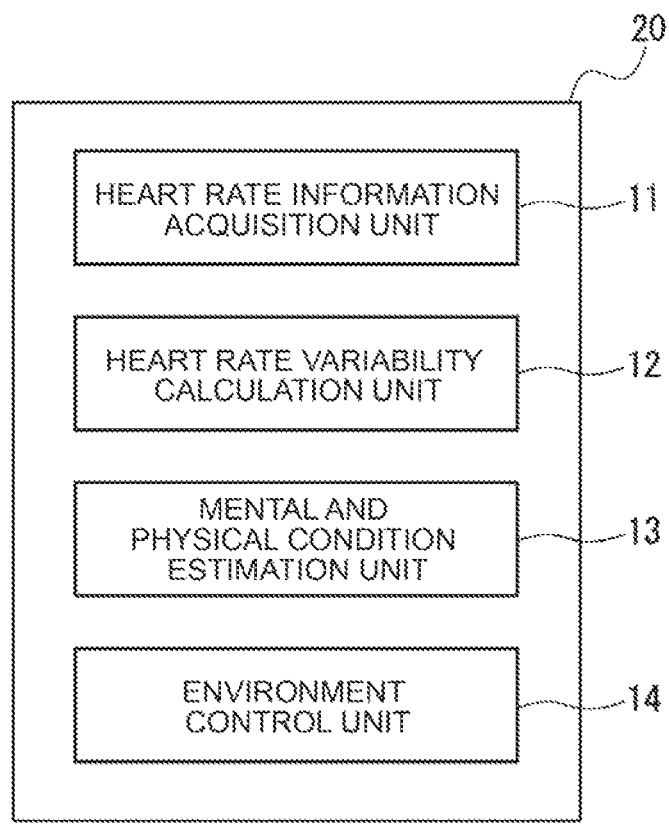
FIG. 5 is a block diagram showing a mental and physical condition estimation system according to a second embodiment.

FIG. 5 is a block diagram showing a mental and physical condition estimation system 20 according to the second embodiment. Hereinafter, the same reference signs are assigned to the same components as those of the mental and physical condition estimation system according to the first embodiment, and only different components will be described.

The environment control unit 14 controls the environment around the subject person based on the estimated mental and physical condition. By controlling the environment around the subject person, the optimal mental and physical condition for the subject person can be achieved. The environment control unit 14 includes a control content determination unit for determining the control content based on the mental and physical condition estimated by the mental and physical condition estimation unit 13. Alternatively, the control content determination unit may be provided separately.

The environment control unit 14 performs control to increase the concentration when the concentration and effort state estimated by the mental and physical condition estimation unit 13 is equal to or less than a predetermined level. As described above, when the value of the VLF or the value of the VLF2 calculated by the heart rate variability calculation unit 12 is smaller than the normal value (threshold value), the mental and physical condition estimation unit 13 estimates that the concentration state of the subject person is low. When the value of the VLF or the value of the VLF2 is smaller than the normal value (threshold value), the environment control unit 14 can perform control to increase the concentration. Details of the control content will be described with reference to FIG. 6.

FIG. 6 is a table showing an example of environment control performed by the environment control unit 14 of the mental and physical condition estimation system according to the second embodiment. As shown in FIG. 6, the concentration state can be increased by controlling hearing, smell, touch, and vision. Each of the control items of hearing, smell, touch, and vision may be used alone for the environment control, or a combination of a plurality of the control items may be used for the environment control.

Specifically, when the control item is hearing, a speaker is installed in an environment around the subject person. The environment control unit 14 performs control so that the sound of leaves rustling in the wind is played in a volume that can be heard by the subject person. When the control item is the smell, the environment control unit 14 performs control so that, for example, the scent of rosemary essential oil reaches the subject person. Other essential oils known to affect the improvement of concentration may also be used. The essential oil may be made into a mist using an aroma diffuser, or may be dropped into a small object such as an aroma stone. Any method may be used as long as the scent of the essential oil is delivered to the subject person.

When the control item is touch, the subject person is seated in a seat that vibrates or a chair with a seating surface that vibrates. The environment control unit 14 obtains a cycle from the frequency of the VLF or the VLF2 of the subject person, and vibrates the seat at the cycle.

When the control item is vision, illumination capable of changing the illuminance is arranged within the range of the field of view of the subject person. The environment control unit 14 changes the illuminance of light. The color of the light may be, for example, blue or the like. The method of changing the illuminance of the light includes a case where the light is caused to blink so that the frequency of the VLF signal of the subject person is synchronized with the illuminance at the same cycle or at a constant multiple thereof, or at the same phase or at a constant multiple thereof, and a case where the light is caused to blink so that the frequency of the VLF signal of the subject person is synchronized with the variance of the illuminance at the same cycle or at a constant multiple thereof, or at the same phase or at a constant multiple thereof.

In "the case where the light is caused to blink so that the frequency of the VLF signal of the subject person is synchronized with the illuminance at the same cycle or at a constant multiple thereof, or at the same phase or at a constant multiple thereof", the illuminance of light is changed randomly. First, the variance of the predetermined illuminance of the illumination to be used may be statistically obtained, and the blinking may be performed so that the frequency of the VLF signal is synchronized with the variance at the same cycle or at a constant multiple thereof, or at the same phase or at a constant multiple thereof. Further, the blinking may be performed so that the amplitude of the frequency of the VLF signal is synchronized with the illuminance of the light at the same cycle or at a constant multiple thereof, or at the same phase or at a constant multiple thereof.

The environment control unit 14 may cause the light to blink using n times the frequency of the VLF signal (n is a natural number of 1 or more) or 1/n times (n is a natural number of 2 or more), rather than using the frequency itself of the VLF signal of the subject person. Since it is known that brain activity plays different roles on the right and left sides, different blinking states may be used on the right side and the left side of the field of view of the subject person when blinking the light. For example, blinking may be performed on the left side with the frequency of the VLF signal of the subject person synchronized with the illuminance, and blinking may be performed on the right side with the frequency of the VLF signal of the subject person synchronized with the variance of the illuminance. The right and left sides may be reversed.

When the fatigue state estimated by the mental and physical condition estimation unit 13 is equal to or higher than a predetermined level, the environment control unit 14 may further perform control to alleviate fatigue. As described above, when the value of the VLF or the value of the VLF1 calculated by the heart rate variability calculation unit 12 is larger than the normal value (threshold value), the mental and physical condition estimation unit 13 estimates that the subject person is fatigued. When the value of the VLF or the value of the VLF1 is larger than the normal value (threshold value), the environment control unit 14 can perform control for alleviating fatigue. An example of the specific control content will be described with reference to FIG. 7.

FIG. 7 is a table showing an example of the environment control performed by the environment control unit of the mental and physical condition estimation system according to the second embodiment. As shown in FIG. 7, the fatigue state can be alleviated by controlling hearing, smell, touch, and vision. As in the control of the concentration state, each of the control items of hearing, smell, touch, and vision may be used alone for the environment control, or a combination of a plurality of the control items may be used for the environment control.

Specifically, when the control item is hearing, a speaker is installed in an environment around the subject person. The environment control unit 14 performs control so that the sound of trickling water by the brook is played in a volume that can be heard by the subject person. When the control item is the smell, the environment control unit 14 performs control so that, for example, the scent of cypress essential oil reaches the subject person. Other essential oils known to be effective for alleviating fatigue may also be used. The essential oil may be made into a mist using an aroma diffuser, or may be dropped into a small object such as an aroma stone. Any method may be used as long as the scent of the essential oil is delivered to the subject person.

When the control item is touch, the subject person is seated in a seat that vibrates or a chair with a seating surface that vibrates. The environment control unit 14 obtains a cycle from the frequency of the HF of the subject person, and vibrates the seat at the cycle.

When the control item is vision, illumination capable of changing the illuminance is arranged within the range of the field of view of the subject person. The environment control unit 14 changes the illuminance of light. The color of the light can be blue. As a method of changing the illuminance of the light, blinking is performed so that the frequency of the VLF signal of the subject person is synchronized with the illuminance.

Next, the mental and physical condition estimation method according to the present embodiment will be described.

Figure 8:
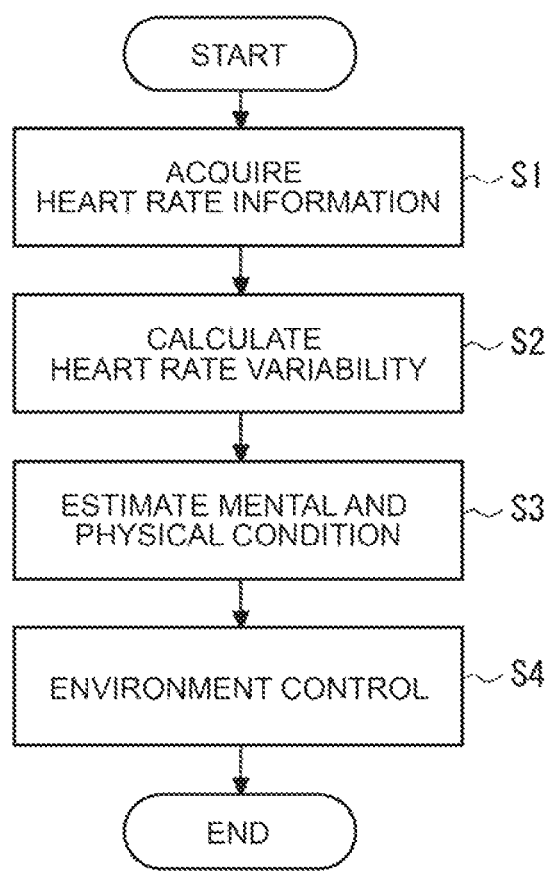
FIG. 8 is a flowchart showing a mental and physical condition estimation method according to the second embodiment.

FIG. 8 is a flowchart showing the mental and physical condition estimation method according to the second embodiment. As shown in FIGS. 5 and 8, the mental and physical condition estimation method according to the present embodiment includes, in addition to steps S1 to S3 of the first embodiment, a step (step S4) in which the environment control unit 14 controls the environment around the subject person based on the estimated mental and physical condition.

A step of determining whether to end the control may be further provided after step 4. For example, the environment control of step S4 may be continued for a predetermined time, or steps S1 to S3 may be executed after the environment control of step S4, and the environment control of step S4 may be repeated until the mental and physical condition of the subject person reaches a desired state.

The mental and physical condition estimation system and the mental and physical condition estimation method according to the present embodiment include the environment control unit that controls the environment around the subject person. By controlling the surrounding environment, the optimal mental and physical condition for the subject person can be achieved. Therefore, a comfortable environment with high productivity, high performance, and low stress can be realized. When the value of the VLF or the value of the VLF2 is smaller than the normal value (threshold value), the environment control unit can perform control to increase the concentration. This makes it possible to increase the concentration when the concentration of the subject person is reduced. When the value of the VLF or the value of the VLF1 is larger than the normal value (threshold value), the environment control unit can perform control for alleviating fatigue. This makes it possible to alleviate fatigue when the subject person is fatigued.

Third Embodiment

The mental and physical condition estimation system according to the present embodiment further includes, in addition to the mental and physical condition estimation system according to the second embodiment, a target setting unit for setting a target of the mental and physical condition. Hereinafter, the mental and physical condition estimation system according to the present embodiment will be described with reference to FIG. 9.

Figure 9:
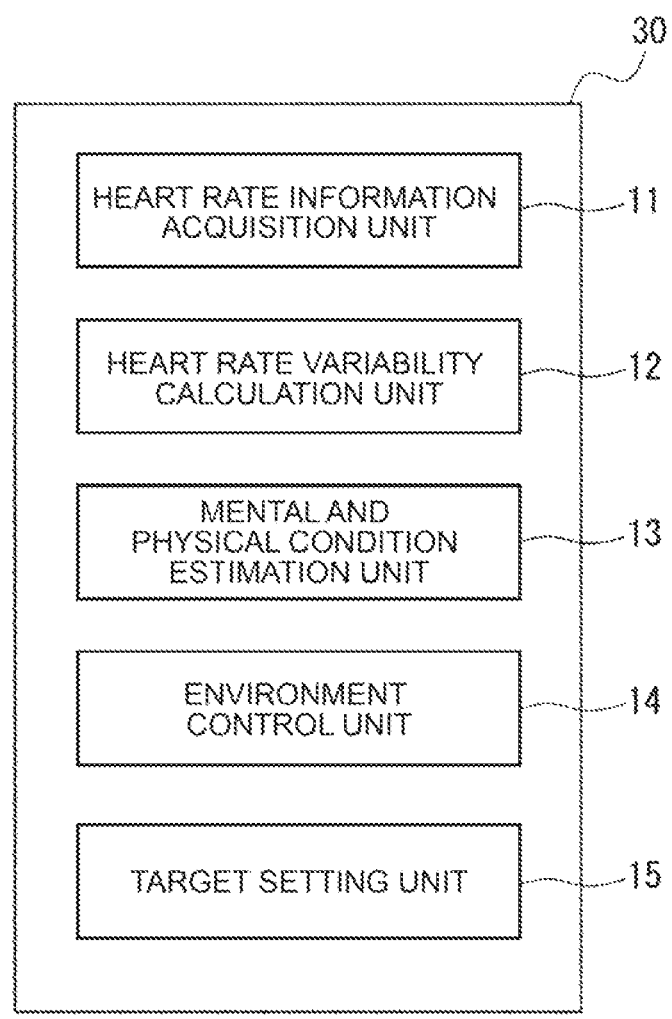
FIG. 9 is a block diagram showing a mental and physical condition estimation system according to a third embodiment.

FIG. 9 is a block diagram showing a mental and physical condition estimation system 30 according to a third embodiment. Hereinafter, the same reference signs are assigned to the same components as those of the mental and physical condition estimation system according to the second embodiment, and only different components will be described.

A target setting unit 15 sets a target mental and physical condition for the subject person. The environment control unit 14 controls the environment around the subject person based on the mental and physical condition of the subject person estimated by the mental and physical condition estimation unit 13 and the set target of the mental and physical condition. When setting the target mental and physical condition for the subject person, the desired mental and physical condition of the subject person may be input to the target setting unit 15, or data in which the mental and physical condition of the subject person estimated by the mental and physical condition estimation unit 13 and the content of the environment control are correlated in advance may be input to the target setting unit 15.

Here, the states (a) to (f) estimated by the mental and physical condition estimation unit 13 described in the first embodiment with reference to FIG. 3 indicate the current state of the subject person. Further, the target mental and physical condition for the subject person set by the target setting unit 15 of the present embodiment is, as an example, the states (a), (c), and (d) among the following states (a) to (f).

(a) Concentration state and uplifting state: large VLF, large LF/HF, less than 20 minutes
(b) Fatigue state: large VLF, large LF/HF, 20 minutes or more
(c) Creative and inspired state: large VLF, large HF
(d) Resting and relaxed state: VLF within range of normal value (threshold value), large HF
(e) Distracted and irritated state: small VLF, large LF/HF
(f) Bored and weary state: small VLF, large HF An example of the specific control content in the case where the target setting unit 15 sets the states (a), (c), and (d) as the target mental and physical condition for the subject person will be described with reference to FIG. 10.

FIG. 10 is a table showing an example of the environment control performed by the environment control unit 14 of the mental and physical condition estimation system according to the third embodiment. As shown in FIG. 10, the mental and physical condition of the subject person can be controlled to states (a), (c), and (d) by controlling temperature, hearing, smell, touch, vision (light), vision (other than light), and wind. Each of the control items of temperature, hearing, smell, touch, vision (light), vision (other than light), and wind may be used alone for the environment control, or a combination of a plurality of the control items may be used for the environment control.

For example, when the mental and physical condition estimated by the mental and physical condition estimation unit 13 is the state (e) or the state (f), the target setting unit 1S sets the target of the mental and physical condition to the state (a) or the state (c), and the environment control unit 14 controls the environment around the subject person such that the mental and physical condition of the subject person is adjusted from the state (e) or the state (f) to the state (a) or the state (c) that is the concentration state. That is, as shown in FIGS. 3 and 10, with the environment control of the space in which the subject person stays, the state of the subject person can be controlled from the state (distraction) with a small value of the VLF to the state (concentration) with a large value of the VLF.

Similarly, when the mental and physical condition estimated by the mental and physical condition estimation unit 13 is any one of the states (c), (d), and (f), the target setting unit 15 sets the target of the mental and physical condition to (a) that is a concentration and uplifting state, and the environment control unit 14 controls the environment around the subject person such that the mental and physical condition of the subject person is adjusted from the states (c), (d), and (f) to the state (a). That is, as shown in FIGS. 3 and 10, with the environment control of the space in which the subject person stays, the state of the subject person can be controlled from the state (relaxed, deactivated, and drowsy) with a large value of the HF to the state (activated) with a large value of the LF/HF.

Further, when the mental and physical condition estimated by the mental and physical condition estimation unit 13 is the state (b) or the state (e), the target setting unit 15 sets the target of the mental and physical condition to the state (c) or the state (d), and the environment control unit 14 controls the environment around the subject person such that the mental and physical condition of the subject person is adjusted from the state (b) or the state (e) to the state (c) or the state (d). That is, as shown in FIGS. 3 and 10, with the environment control of the space in which the subject person stays, the state of the subject person can be controlled from the state (nervous, fatigued, and activated) with a large value of the LF/HF to the state (inspired and relaxed) with a large value of the HF.

As a specific example, when the subject person wants to relax, the resting and relaxed state of (d) is input to the target setting unit 15, for example. When the subject person wants to concentrate on work or study, the concentration state of (a) is input to the target setting unit 15. When the concentration state of (a) is continued for 20 minutes or more, since the fatigue state of (b) occurs, the surrounding environment is controlled so as to be adjusted to (c) or (d). After the state (c) or the state (d) has elapsed for about 20 minutes, the environment around the subject person is controlled so as to be adjusted to the concentration state (a) again. This series of controls may be input to the target setting unit as desired by the subject person, or may be input to the target setting unit 15 in advance so as to repeat the above-mentioned environment control of (a) and (c) or (d). When the subject person performs creative work or wants to be inspired, the creative and inspired state of (c) is input to the target setting unit. In order to increase the concentration of the subject person and make the mental and physical condition difficult to fatigue, the control content is determined so that the VLF increases and the LF/HF does not increase.

The specific control content performed by the environment control unit 14 is the same as that in the first embodiment for hearing, smell, touch, and vision (light). Here, the temperature and the wind will be described. As shown in FIG. 10, when the control item is temperature, the environment control unit 14 controls the temperature of the space in which the subject person stays. When the control item is vision (other than light), the environment control unit 14 performs control to place plants within the range of the field of view of the subject person or to play an image of plants.

When the control item is wind, the environment control unit 14 causes artificial wind to blow into the space in which the subject person stays. The environment control unit 14 changes the wind speed in synchronization with the VLF signal of the subject person. The method of changing the wind speed includes a case where the wind speed is changed so that the frequency of the VLF signal of the subject person is synchronized with the average value of the wind speed at the same cycle or at a constant multiple thereof, or at the same phase or at a constant multiple thereof, and a case where the wind speed is changed so that the frequency of the VLF signal of the subject person is synchronized with the variance of the wind speed at the same cycle or at a constant multiple thereof, or at the same phase or at a constant multiple thereof.

In the "case where the wind speed is changed so that the frequency of the VLF signal of the subject person is synchronized with the average value of the wind speed at the same cycle or at a constant multiple thereof, or at the same phase or at a constant multiple thereof", first, the average value of the wind speed of the wind generated by a device capable of blowing artificial wind during a predetermined time is obtained. This is the case where the wind speed is further changed from the average value in accordance with the VLF signal of the subject person.

In "case where the wind speed is changed so that the frequency of the VLF signal of the subject person is synchronized with the variance of the wind speed at the same cycle or at a constant multiple thereof, or at the same phase or at a constant multiple thereof", the wind speed is changed randomly. First, the variance of the wind speed at a predetermined wind speed generated by the device capable of blowing artificial wind may be statistically obtained, and the wind speed may be changed so that the frequency of the VLF signal is synchronized with the variance at the same cycle or at a constant multiple thereof, or at the same phase or at a constant multiple thereof. Further, the wind speed may be changed so that the amplitude of the frequency of the VLF signal is synchronized with the wind speed at the same cycle or at a constant multiple thereof, or at the same phase or at a constant multiple thereof.

The environment control unit 14 may change the wind speed using n times the frequency of the VLF signal (n is a natural number of 1 or more) or 1/n times (n is a natural number of 2 or more), rather than using the frequency itself of the VLF signal of the subject person. Since it is known that brain activity plays different roles on the right and left sides, different wind speeds may be used on the right side and the left side of the subject person. For example, the wind speed may be changed on the left side with the frequency of the VLF signal of the subject person synchronized with the wind speed, and the wind speed may be changed on the right side with the frequency of the VLF signal of the subject person synchronized with the variance of the wind speed. The right and left may be reversed.

In the case where the control is performed so that the subject person is in the concentration state of the state (a) or the state (c), the environment control unit 14 changes the wind speed at the frequency of the VLF of the subject person. Similarly, in the case where the control is performed so that the subject person is in the concentration and uplifting state of the state (a), the environment control unit 14 changes the wind speed at the frequency of the LF of the subject person.

The target setting unit 15 according to the present embodiment may set a target based on a predetermined schedule. For example, the target mental and physical condition of each time zone may be set according to the schedule of the subject person so that the mental and physical condition of the subject person becomes the target mental and physical condition in the set time zone. Alternatively, the target setting unit 15 may estimate an optimal mental and physical condition for each timezone in which the schedule is performed in accordance with the content of the schedule of the subject person, and may set the optimal mental and physical condition as the target mental and physical condition.

When the target setting unit 15 sets a target based on a predetermined schedule, the target can be automatically set based on the schedule of the subject person even when the subject person does not set the target by himself/herself.

The mental and physical condition estimation system according to the present embodiment may further include an environment information acquisition unit for acquiring environment information around the subject person. The environment information acquisition unit may acquire environment information around the subject person in advance. The environment information acquisition unit may acquire the environment information in parallel with the acquisition of the heart rate information, the calculation of the heart rate variability, and the estimation of the mental and physical condition. Based on the acquired environment information, the environment control unit can control the environment around the subject person so that the mental and physical condition of the subject person becomes the target mental and physical condition for the subject person. With the environment information acquisition unit, it is possible to control the mental and physical condition with higher accuracy.

Further, in order to improve the accuracy of estimation of the mental and physical condition of the subject person and to improve the effect of the environment control, a database in which various pieces of information are registered may be created and used for target setting of the mental and physical condition, estimation of the mental and physical condition, and the environment control. The database may store, for example, data including personal identification information, environment information, biometric indices, mental and physical condition estimation results, target input information, environment control content, and the mental and physical condition after the environment control. Furthermore, variability such as intraday variation and seasonal variation of the mental and physical condition, change in the mental and physical condition due to the environment control, and reactivity may be registered in the database.

Next, the mental and physical condition estimation method according to the present embodiment will be described.

Figure 11:
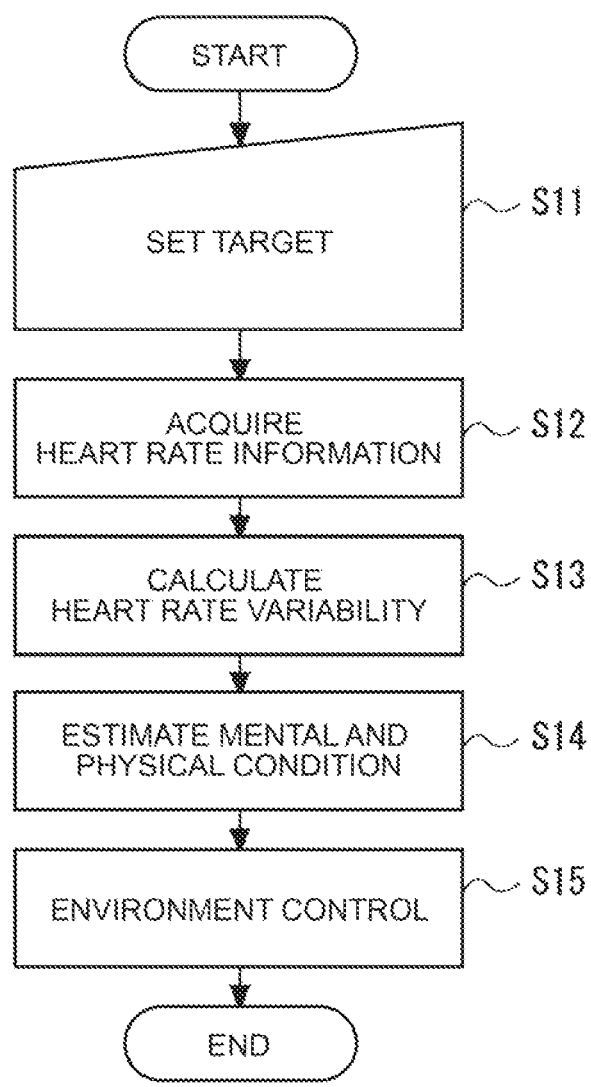
FIG. 11 is a flowchart showing a mental and physical condition estimation method according to the third embodiment.

FIG. 11 is a flowchart showing a mental and physical condition estimation method according to the third embodiment. As shown in FIGS. 9 and 11, the mental and physical condition estimation method according to the present embodiment further includes, in addition to steps S1 to S4 of the second embodiment (steps S12 to S15 of the present embodiment), a step (step S11) in which the target setting unit 15 sets the target of the mental and physical condition of the subject person.

A step of determining whether to end the control may be further provided after step S15. For example, steps S12 to S14 may be executed after the environment control of step S15, and the environment control of step S15 may be repeated until the mental and physical condition of the subject person becomes the set target state. The information registered in the database may be used for the target setting of the mental and physical condition, the estimation of the mental and physical condition, and the environment control.

The mental and physical condition estimation system and the mental and physical condition estimation method according to the present embodiment further include the target setting unit for setting a target of the mental and physical condition of the subject person. With the target setting unit, it is possible to adjust the mental and physical condition of the subject person to a desired mental and physical condition as a target.

Other Embodiments

The mental and physical condition estimation system of the present disclosure can realize any processing for estimating the mental and physical condition when a processor such as a central processing unit (CPU) reads and executes a computer program stored in a memory.

In the examples described above, the program can be stored using various types of non-transitory computer-readable media and supplied to a computer. The non-transitory computer-readable media include various types of tangible storage media. Examples of the non-transitory computer-readable media include magnetic storage media (e.g. flexible disks, magnetic tapes, hard disk drives), magneto-optical storage media (e.g. magneto-optical disks), compact disc read-only memory (CD-ROM), compact disc recordable (CD-R), compact disc rewritable (CD-R/W), and semiconductor memory (e.g. mask ROM, programmable ROM (PROM), erasable PROM (EPROM), flash ROM, random access memory (RAM)). The program may also be supplied to the computer by various types of transitory computer-readable media. Examples of the transitory computer-readable media include electrical signals, optical signals, and electromagnetic waves. The transitory computer-readable media can supply the program to the computer via a wired communication path such as an electric wire and an optical fiber, or a wireless communication path.

Hereinafter, the present disclosure will be specifically described based on examples with reference to FIGS. 12 to 16, but the present disclosure is not limited to these examples only.

First Example

In this example, a fatigue task experiment was performed for 37 subject persons, and the mental and physical condition before and after the task was examined. The VLF, the ln(LF/HF) that is an index used conventionally, and fatigue feeling subjective evaluation (VAS) were used as indices for examining the mental and physical condition. As the fatigue task, the PVT and the n-back task were performed.

First, the heart rate information acquisition unit included in the mental and physical condition estimation system according to the first embodiment acquired the heart rate information in the resting state for 5 minutes, and the heart rate variability calculation unit calculated the normal value (threshold value) of the value of the heart rate variability in the resting state. Subsequently, the PVT (first time) was performed for 5 minutes followed by the n-back task (3-back task) for 20 minutes. After the n-back task, the PVT (second time) was performed for 5 minutes. Subsequently, the heart rate information acquisition unit included in the mental and physical condition estimation system acquired an electrocardiogram as the heart rate information for 5 minutes, and the heart rate variability calculation unit calculated the value of the ln(LF/HF) and the value of the VLF, and obtained the average value between the subject persons. In parallel, the fatigue feeling subjective evaluation (VAS) was also performed before and after the fatigue task.

Figure 12:
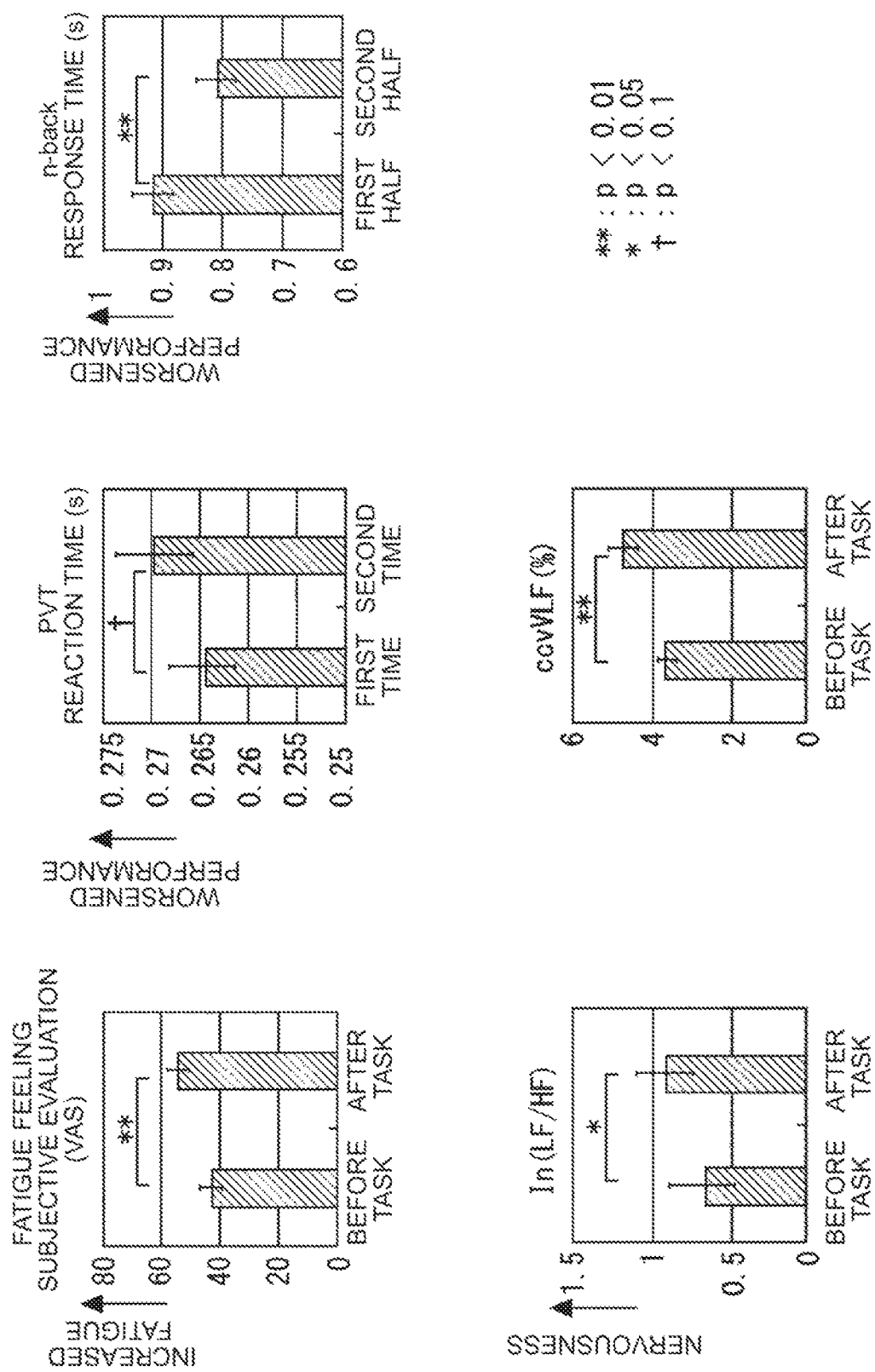
FIG. 12 are graphs showing a result of a fatigue feeling subjective evaluation before and after a fatigue task experiment according to a first example, a result of PVT reaction time, a result of n-back response time, a result of ln(LF/HF), and a result of ccvVLF (%)

FIG. 12 are graphs showing a result of the fatigue feeling subjective evaluation before and after the fatigue task experiment according to the first example, a result of the PVT reaction time, a result of the n-back response time, a result of the ln(LF/HF), and a result of the ccvVLF (%). All graphs show corresponding t-test results. The sign ** represents $p<0.01$, * represents $p<0.05$, and † represents $p<0.1$, each indicating significant differences or significant tendencies. The vertical axes of FIG. 12 show, in order from the upper left, the result of the fatigue feeling subjective evaluation (VAS), the result of the PVT response time, and the result of the n-back response time, and show, in order from the lower left, the result of the ln(LF/HF) and the result of the ccvVLF (%).

As shown in the upper left of FIG. 12, the result of the VAS significantly increased after the task as compared with before the task. An increase in the value of the VAS indicates an increase in fatigue. This indicates that the subject person was fatigued due to the n-back task.

As shown in the upper center of FIG. 12, the result of the PVT reaction time tended to increase in the second time performed after the n-back task as compared with the first time of the PVT performed before the n-back task. Increased PVT response time indicates worse performance. The worsening of the performance in the PVT indicates that the subject person was fatigued due to the n-back task.

As shown in the upper right of FIG. 12, for the n-back response time, of the n-back task performed for 20 minutes, the first half was defined as the time from 2 minutes to 8 minutes after the start of the n-back task, and the second half was defined as the time from 14 minutes to 20 minutes after the start of the n-back task. The n-back response time decreased significantly in the second half compared to the first half. A decrease in the n-back response time indicates an improvement in performance. In other words, it was confirmed that the subject person made an effort to deal with the n-back task and concentrated on the task.

As shown in the lower left of FIG. 12, the average value of the ln(LF/HF), which is regarded as an index of mental fatigue in the related art, also increased significantly after the task as compared with the average value before the task.

The coefficient component of variance VLF (ccvVLF, component variation factor VLF; shown in the lower right of FIG. 12 is obtained by correcting the power value of the component VLF by the average heart rate interval (RR interval). That is, the formula "ccvVLF (%)=100×√(VLF power)/average heart rate interval" holds. As shown in FIG. 12, the ccvVLF also increased significantly after the task as compared with before the task.

Figure 13:
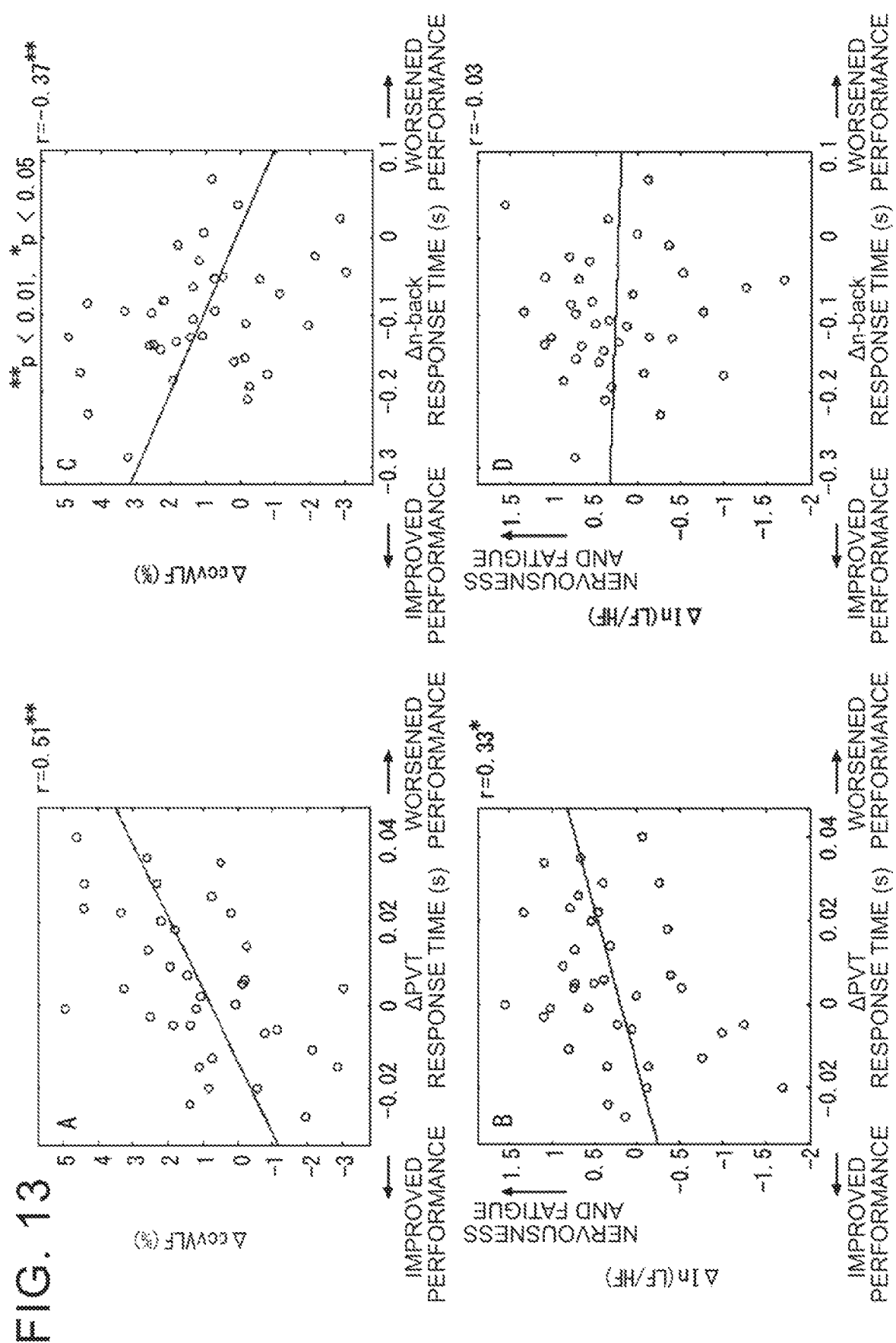
FIG. 13 are graphs showing results of a correlation analysis of a performance in the fatigue task experiment according to the first example and the amount of change before and after the fatigue task experiment of the heart rate variability.

FIG. 13 are graphs showing a result of a correlation analysis of a performance in the fatigue task experiment according to the first example and the amount of change in the heart rate variability before and after the fatigue task experiment. The sign ** represents $p<0.01$ and * represents $p<0.05$, each indicating a significant correlation. The plots show the task performance of the 37 subject persons and the amount of change in the ccvVLF or the ln(LF/HF) that indicates the mental and physical condition before and after the fatigue task.

The PV reaction time means the reaction time for the indicated task. The ΔPVT reaction time (seconds) on the horizontal axes of graphs A and B shown in FIG. 13 is the difference between the PVT reaction time before performing the n-back task and the PVT reaction time after performing the n-back task. For example, when the PVT reaction time after performing the n-back task becomes shorter than the PVT reaction time before performing the n-back task, the ΔPVT reaction time becomes a negative value, and the performance is improved. On the other hand, when the PVT reaction time after performing the n-back task becomes longer than the PVT reaction time before performing the n-back task, the ΔPVT reaction time becomes a positive value, and the performance is deteriorated. In other words, the more positive the value of the ΔPVT response time is, the more fatigued the subject person is.

The Δn-back response time (seconds) on the horizontal axes of graphs C and D shown in FIG. 13 is the difference between the time required for responding to the task in the first half (after 2 minutes to 8 minutes from the task start) and the time required for responding to the task in the second half (after 14 minutes to 20 minutes from the task start), of the n-back task performed for 20 minutes. For example, when the response time required for the second half of the n-back task becomes shorter than the response time required for the first half of the n-back task for the n-back task response time, the Δn-back response time becomes a negative value, and the performance is improved. On the other hand, when the response time required for the second half of the n-back task becomes longer than the response time required for the first half of the n-back task, the Δn-back response time becomes a positive value, and the performance is deteriorated. In other words, the more negative the value of the Δn-back response time is, the more concentrated and effortful the subject person is.

In order to confirm whether there is a correlation between the ΔPVT response time and the Δn-back response time, which are the results of the fatigue task experiments, and the ccvVLF indicating the mental and physical condition and the ln(LF/HF) which has been used conventionally, Pearson's product rate correlation coefficients were obtained.

The ΔccvVLF on the vertical axes of graphs A and C shown in FIG. 13 is the difference between the values of the ccvVLF indicating the mental and physical conditions before and after the fatigue task experiment. The Δ ln(LF/HF) on the vertical axes of graphs B and D is the difference between the values of the ln(LF/HF) indicating the mental and physical conditions before and after the fatigue task experiment.

The correlation coefficients for graphs A to D of FIG. 13, i.e., the following (A) to (D), are as follows:
  (A) correlation coefficient between ΔPVT response time (s) and ΔccvVLF (%): r=0.51**
  (B) correlation coefficient between ΔPVT response time (s) and Δ ln(LF/HF): r=0.33*
  (C) correlation coefficient between Δn-back response time (s) and ΔccvVLF (%): r=−0.37*
  (D) correlation coefficient between Δn-back response time (s) and Δ ln(LF/HF): r=−0.03

The correlation coefficient values of both (A) and (B) for the correlation of the ΔPVT reaction time showed a positive correlation. On the other hand, a result was obtained in which the value of the correlation coefficient (A) (r=0.51) between the ΔccvVLF was larger than the value of the correlation coefficient (B)(r=0.33) between the Δ ln(LF/HF), which is conventionally known as an index of mental fatigue. The result indicates that the ΔccvVLF correlates more with the ΔPVT response time than the Δ ln(LF/HF) does, which is conventionally known as an index of mental fatigue.

Regarding the correlation with the Δn-back response time, the graph C of FIG. 13 and the value of the correlation coefficient (C) (r=−0.37) showed that the ΔccvVLF has a negative correlation with the Δn-back response time. Further, referring to the graph C of FIG. 13, a result was obtained in which, when the performance in the n-back task is improved, that is, when the subject person is more concentrated and effortful, the value of the ccvVLF is also increased. On the other hand, from the value of the correlation coefficient (D) (r=−0.03), no correlation was found between the Δ ln(LF/HF), which is conventionally known as an index of mental fatigue, and the Δn-back response time.

The results in FIG. 13 indicate that the ccvVLF has a positive correlation with the ΔPVT response time and has a negative correlation with the Δn-back response time. As described above, the more positive the value of the ΔPVT response time is, the more fatigued the subject person is, and the more negative the value of the Δn-back response time is, the more concentrated and effortful the subject person is. Therefore, it has been shown that the ccvVLF, i.e., the VLF that has a positive correlation with the ΔPVT response time and has a negative correlation with the Δn-back response time, can be used to estimate the fatigue state and the concentration and effort state.

Second Example

In this example, a fatigue task was performed for eight subject persons, and the environment control was performed. Comparison and correlation analysis were performed on the average value of the mental and physical condition before the fatigue task and the average value of the mental and physical condition after the fatigue task and also the environment control. Multiple comparisons by two-way repeated measures analysis-of-variance and Holm methods were used to compare the average values.

In this example, the VLF and the fatigue/arousal subjective evaluation indices Roken Arousal scale (RAS) are used as the indices of mental and physical conditions. In this example, "attention concentration difficulty" which is one of the items of the RAS is used as an evaluation index. The heart rate information acquisition unit included in the mental and physical condition estimation system according to the second embodiment acquired the heart rate information in the resting state, and the heart rate variability calculation unit calculated the normal value (threshold value) of the value (VLF) of the heart rate variability in the resting state. Subsequently, virtual reality (VR) games were played as a fatigue task for 10 minutes. Subsequently, the environment control unit included in the mental and physical condition estimation system controlled the environment around the subject person.

As the environment control item in this example, vision (other than light) described in FIG. 10, that is, plants were used. In this example, eight subject persons participated in the experiment for four days each, performed one experiment of the four environments each day, and stayed in each environment for 20 minutes. The heart rate information acquisition unit included in the mental and physical condition estimation system acquired an electrocardiogram between κ minutes and 5 minutes from the start of stay in each environment as the heart rate information, and the heart rate variability calculation unit calculated the value (VLF) of the heart rate variability. In parallel, the subjective evaluation "attention concentration difficulty" was performed in the resting state before the fatigue task and 20 minutes after the start of stay in each environment after the fatigue task.

Figure 14:
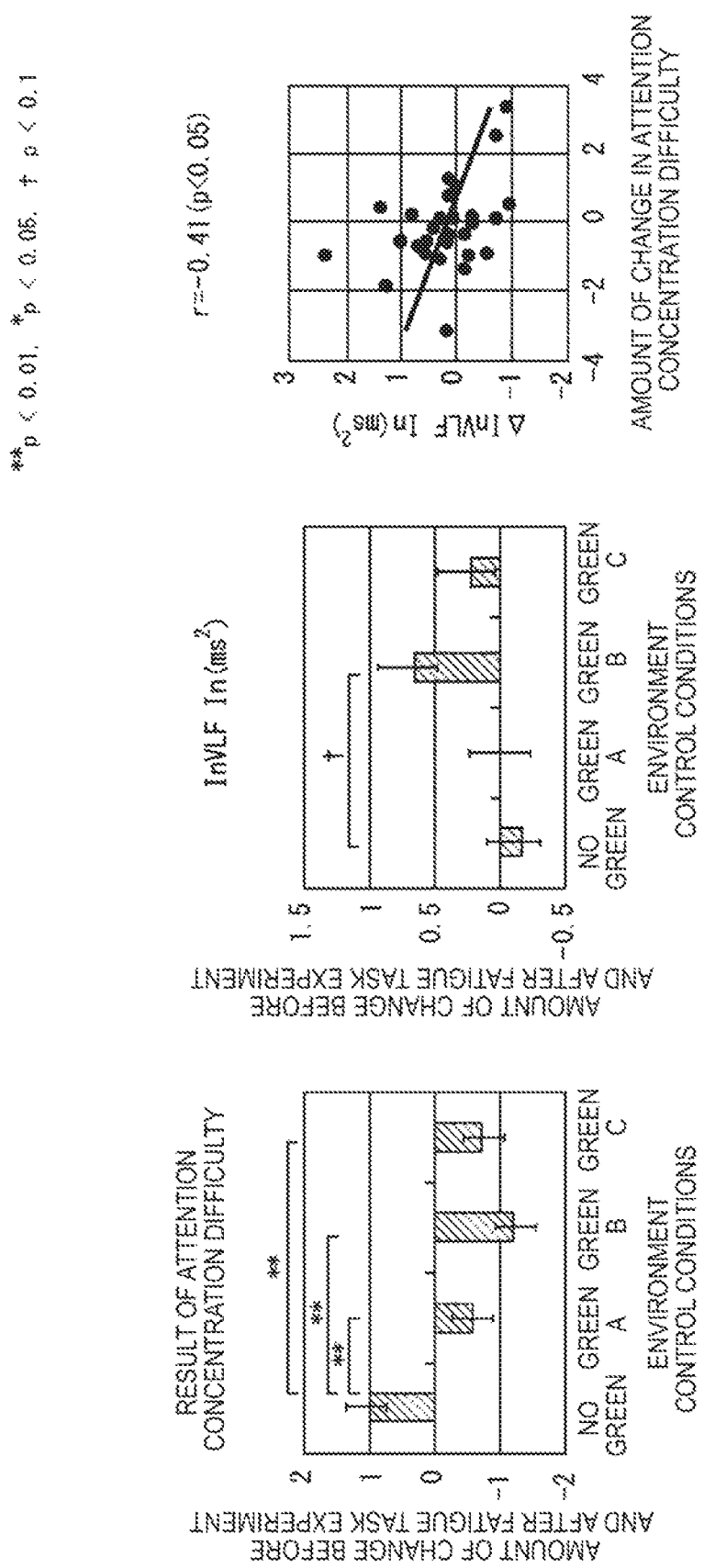
FIG. 14 are graphs showing results of comparison of the average value of VLF for a subjective evaluation "attention concentration difficulty" according to a second example and a correlation analysis thereof.

FIG. 14 are graphs showing the results of comparison of the average value of the VLF for the subjective evaluation "attention concentration difficulty" according to the second example and a correlation analysis thereof. The left and center graphs show the results of multiple comparisons by the Holm method. The sign ** represents p<0.01, * represents p<0.05, and † represents p<0.1, indicating significant differences or significant tendencies. The horizontal axes in the left and center graphs show the environment conditions. "No Green" is an environment in which plants are not in the range that can be seen by the subject person.

"Green A" is an environment in which plants with rounder and smaller leaves compared to Green C are placed within the range of the field of view of the subject person. As shown in FIGS. 3 and 10, Green A has an effect for creativity, inspiration, resting, and relaxing.

"Green B" is an environment in which plants with elongated leaves are placed within the range of the field of view of the subject person. As shown in FIGS. 3 and 10, Green B has an effect of increasing concentration.

"Green C" is an environment in which plants with larger leaves compared to Green A are placed within the range of the field of view of the subject person. As shown in FIGS. 3 and 10, Green C has an effect of increasing activeness.

The "amount of change before and after fatigue task experiment" on the vertical axis in the left graph of FIG. 14 indicates the difference between the result of the subjective evaluation "attention concentration difficulty" performed before the fatigue task is performed and the result of the subjective evaluation "attention concentration difficulty" performed 20 minutes after the start of stay in the environment. The amount of change shown in the left graph is the result obtained by removing the influence of the state before performing the fatigue task by the analysis of covariance. The amount of change in the subjective evaluation "attention concentration difficulty" means that the more negative the value is, the more concentrated the subject person is.

Similarly, the "amount of change before and after fatigue task experiment" on the vertical axis in the center graph of FIG. 14 indicates the difference between the value of the lnVLF calculated as the normal value (threshold value) in the resting state before performing the fatigue task and the value of the lnVLF between 0 minutes and 5 minutes from the start of the stay in the environment. The amount of change shown in the center graph is the result obtained by removing the influence of the state before performing the fatigue task by the analysis of covariance.

As shown in the left graph of FIG. 14, the value of the amount of change in the subjective evaluation "attention concentration difficulty" became the most negative when the subject person stayed in the environment of Green B. That is, when the subject person stayed in the environment of Green B, the subject person was able to increase concentration by plants with elongated leaves placed in the environment.

Further, as shown in the center graph of FIG. 14, the result was obtained that when the subject person stayed in the environment of Green B, the amount of change in the VLF is the largest compared with the environment with no Green. Subsequently, as shown in the right graph, a correlation analysis was performed between the amount of change in the subjective evaluation "attention concentration difficulty" and the amount of change in the VLF. The correlation coefficient between the amount of change in the subjective evaluation "attention concentration difficulty" and the $\Delta$ lnVLFln($ms^2$) was $r=-0.41$ ($p<0.05$), and a significant correlation was found between the amount of change in the subjective evaluation "attention concentration difficulty" and the $\Delta$ lnVLFln($ms^2$).

As described above, since there is a correlation between the amount of change in the subjective evaluation "attention concentration difficulty" indicating the concentration state and the VLF, it is shown that the VLF can be used for estimation of the concentration state.

Third Example

In this example, a fatigue task experiment was performed for 37 subject persons, and the mental and physical condition before and after the task was examined. The VLF1 and the VLF2 were used as indices of mental and physical condition examination. As the fatigue task, the PVT and the n-back task were performed.

First, the heart rate information acquisition unit included in the mental and physical condition estimation system according to the first embodiment acquired the heart rate information in the resting state for 5 minutes, and the heart rate variability calculation unit calculated the normal value (threshold value) of the value of the heart rate variability (the values of the VLF1 and the VLF2) in the resting state. Subsequently, the PVT was performed for 5 minutes followed by the n-back task (3-back task) for 20 minutes. After the n-back task, the PVT was performed again for 5 minutes. Subsequently, the heart rate information acquisition unit included in the mental and physical condition estimation system acquired an electrocardiogram as the heart rate information for 5 minutes, and the heart rate variability calculation unit calculated the value of the VLF1 and the value of the VLF2, and obtained the average value between the subject persons.

Figure 15:
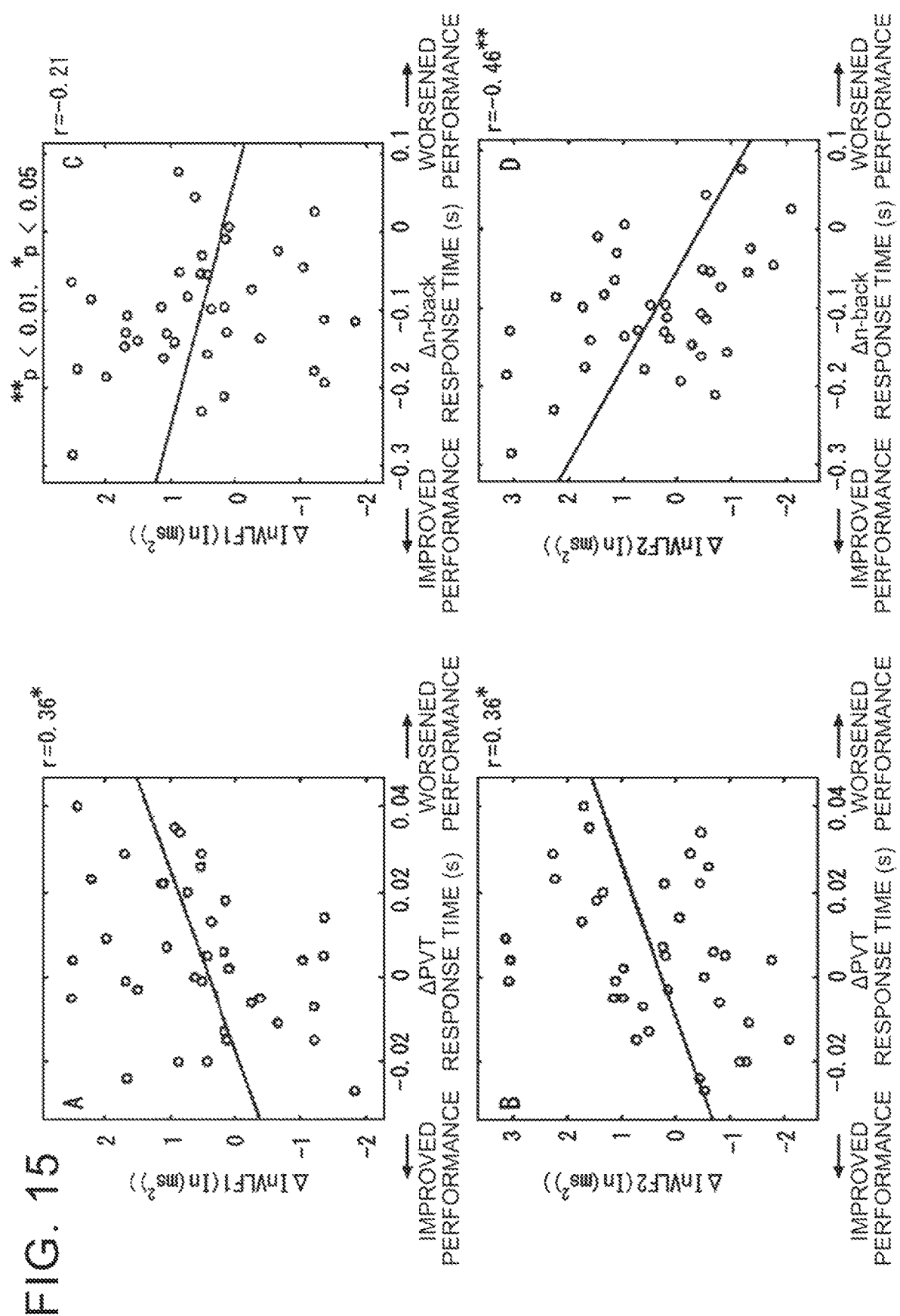
FIG. 15 are graphs showing results of a correlation analysis of a performance in the fatigue task experiment according to a third example and the amount of change before and after the fatigue task experiment of the heart rate variability.

FIG. 15 are graphs showing a result of a correlation analysis of a performance in the fatigue task experiment according to the third example and the amount of change in the heart rate variability before and after the fatigue task experiment. The plots show the task performance of the 37 subject persons and the amount of change in the lnVLF1 or the lnVLF2 that indicates the mental and physical condition before and after the fatigue task. The sign ** represents $p<0.01$ and * represents $p<0.05$, each indicating a significant correlation.

The PVT reaction time means the reaction time for the indicated task. The $\Delta$PVT reaction time (seconds) on the horizontal axes of graphs A and B shown in FIG. 15 is the difference between the PVT reaction time before performing the n-back task and the PVT reaction time after performing the n-back task. For example, when the PVT reaction time after performing the n-back task becomes shorter than the PVT reaction time before performing the n-back task, the $\Delta$PVT reaction time becomes a negative value, and the performance is improved. In other words, the more negative the value of the $\Delta$PVT response time is, the more likely that the subject person is in the concentration and effort state. On the other hand, when the PVT reaction time after performing the n-back task becomes longer than the PVT reaction time before performing the n-back task, the $\Delta$PVT reaction time becomes a positive value, and the performance is deteriorated. In other words, the more positive the value of the $\Delta$PVT response time is, the more fatigued the subject person is.

The $\Delta$n-back response time (seconds) on the horizontal axes of graphs C and D shown in FIG. 15 is the difference between the time required for responding to the task in the first half (after 2 minutes to 8 minutes from the task start) and the time required for responding to the task in the second half (after 14 minutes to 20 minutes from the task start), of the n-back task performed for 20 minutes. For example, when the response time required for the second half of the n-back task becomes shorter than the response time required for the first half of the n-back task for the n-back task response time, the $\Delta$n-back response time becomes a negative value, and the performance is improved. On the other hand, when the response time required for the second half of the n-back task becomes longer than the response time required for the first half of the n-back task, the $\Delta$n-back response time becomes a positive value, and the performance is deteriorated. In other words, the more negative the value of the $\Delta$n-back response time is, the more concentrated and effortful the subject person is.

In order to confirm whether there is a correlation between the $\Delta$PVT response time and the $\Delta$n-back response time, which are the results of the fatigue task experiments, and the amount of change in the lnVLF1 and the amount of change in the lnVLF2 indicating the mental and physical condition, Pearson's product rate correlation coefficients were obtained.

The $\Delta$ lnVLF1 on the vertical axes of graphs A and C shown in FIG. 15 is the difference between the values of the lnVLF1 indicating the mental and physical conditions before and after the fatigue task experiment. The $\Delta$ lnVLF2 on the vertical axes of graphs B and D is the difference between the values of the lnVLF2 indicating the mental and physical conditions before and after the fatigue task experiment.

The correlation coefficients for graphs A to D of FIG. 15, i.e., the following (A) to (D), are as follows:
- (A) correlation coefficient between ΔPVT response time (s) and Δ lnVLF1: r=0.36*
- (B) correlation coefficient between ΔPVT response time (s) and Δ lnVLF2: r=0.36*
- (C) correlation coefficient between Δn-back response time (s) and Δ lnVLF1: r=−0.21
- (D) correlation coefficient between Δn-back response time (s) and Δ lnVLF2: r=−0.46**

From the values of the correlation coefficients of (A) and (B), both the VLF1 and the VLF2 showed similar correlations with the ΔPVT response time. The VLF1 had a high positive correlation with the ΔPVT response time, and the value of the VLF1 increased when the PVT response performance deteriorated due to fatigue.

For the correlation with the Δn-back response time, the value of the correlation coefficient (C) (r=−0.21) showed that the correlation of the VLF1 with the Δn-back response time was hardly observed. On the other hand, the value of the correlation coefficient (D) (r=−0.46) showed that the VLF2 has a significant correlation with the Δn-back response time. Further, referring to the graph D of FIG. 15, a result was obtained in which, when the performance in the n-back task is improved, that is, when the subject person is more concentrated and effortful, the value of the VLF2 is also increased. When the result of the VLF of the first example was compared with the result of the VLF2 of this example, the VLF2 was had a more negative correlation with the N-back response times than the VLF did.

The results in FIG. 15 indicate that the VLF1 and the VLF2 have correlations with the ΔPVT response time and the VLF2 has a negative correlation with the Δn-back response time. As described above, the more positive the value of the ΔPVT response time is, the more fatigued the subject person is, and the more negative the value of 1.5 the Δn-back response time is, the more concentrated and effortful the subject person is. It was shown that the VLF1 that has a positive correlation with the ΔPVT response time can be used for estimation of the fatigue state. It has also been shown that the VLF2 that has a positive correlation with the ΔPVT response time and has a negative correlation with the Δn-back response time can be used to estimate the fatigue state and the concentration and effort state. Therefore, it was shown that the fatigue state and the concentration and effort state can be estimated by distinguishing the states from each other by evaluating the combination of the VLF1 and the VLF2.

Fourth Example

In this example, a fatigue task was performed for eight subject persons, and the environment control was performed. Comparison and correlation analysis were performed on the average value of the mental and physical condition before the fatigue task and the average value of the mental and physical condition after the fatigue task and also the environment control. Multiple comparisons by two-way repeated measures analysis-of-variance and Holm methods were used to compare the average values.

In this example, the VLF2 and the subjective evaluation "attention concentration difficulty", which is one of the items of the RAS, were used as the index of the mental and physical condition. The heart rate information acquisition unit included in the mental and physical condition estimation system according to the second embodiment acquired the heart rate information in the resting state, and the heart rate variability calculation unit calculated the normal value (threshold value) of the value (VLF2) of the heart rate variability in the resting state. Subsequently, virtual reality (VR) games were played as a fatigue task for 10 minutes. Subsequently, the environment control unit included in the mental and physical condition estimation system controlled the environment around the subject person.

As the environment control item in this example, vision (other than light) described in FIG. 10, that is, plants were used. In this example, eight subject persons participated in the experiment for four days each, performed one experiment of the four environments each day, and stayed in each environment for 20 minutes. The heart rate information acquisition unit included in the mental and physical condition estimation system acquired an electrocardiogram between 0 minutes and 5 minutes from the start of stay in each environment as the heart rate information, and the heart rate variability calculation unit calculated the value (VLF2) of the heart rate variability. In parallel, the subjective evaluation "attention concentration difficulty" was performed in the resting state before the fatigue task and 20 minutes after the start of stay in each environment after the fatigue task.

FIG. 16 are graphs showing the results of comparison of the average value of the VLF2 for the subjective evaluation "attention concentration difficulty" according to the fourth example and a correlation analysis thereof. The horizontal axes in the left and center graphs show the environment conditions. The environment conditions of "no Green", "Green A", "Green B", and "Green C" are as described in the second example. The left and center graphs show the results of multiple comparisons by the Holm method. The sign ** represents p<0.01 and * represents p<0.05, each indicating a significant difference.

The "amount of change before and after fatigue task experiment" on the vertical axis in the left graph of FIG. 16 indicates the difference between the result of the subjective evaluation "attention concentration difficulty" performed before the fatigue task is performed and the result of the subjective evaluation "attention concentration difficulty" performed 20 minutes after the start of stay in the environment. The amount of change shown in the left graph is the result obtained by removing the influence of the state before performing the fatigue task by the analysis of covariance. The amount of change in the subjective evaluation "attention concentration difficulty" means that the more negative the value is, the more concentrated the subject person is.

Similarly, the "amount of change before and after fatigue task experiment" on the vertical axis in the center graph of FIG. 16 indicates the difference between the value of the lnVLF2 ln(ms$^2$) calculated as the normal value (threshold value) in the resting state before the fatigue task and the value of the lnVLF2 ln(ms$^2$) between 0 minutes and 5 minutes from the start of the stay in the environment. The amount of change shown in the center graph is the result obtained by removing the influence of the state before performing the fatigue task by the analysis of covariance.

The left graph of FIG. 16 is the same as the left graph of FIG. 14. As shown in FIG. 16, the value of the amount of change in the subjective evaluation "attention concentration difficulty" became the most negative when the subject person stayed in the environment of Green B. That is, when the subject person stayed in the environment of Green B, the subject person was able to increase concentration by plants with elongated leaves placed in the environment.

In addition, as shown in the center graph of FIG. 16, the result was obtained that the change in the VLF2 was the largest in the environment of Green B. Subsequently, as shown in the right graph, a correlation analysis was performed between the amount of change in the subjective evaluation "attention concentration difficulty" and the amount of change in the VLF2. The correlation coefficient between the amount of change in the subjective evaluation "attention concentration difficulty" and the Δ lnVLF2 ln(ms$^2$) was r=−0.34 (p<0.1) and a correlation tendency was found between the amount of change in the subjective evaluation "attention concentration difficulty" and the Δ lnVLF2 ln(ms$^2$).

As described above, since there is a correlation between the amount of change in the subjective evaluation "attention concentration difficulty" indicating the concentration state and the VLF2, it is shown that the VLF2 can be used for estimation of the concentration state.

Note that, the present disclosure is not limited to the above embodiments, and can be appropriately modified without departing from the spirit.

What is claimed is:

1. A mental and physical condition estimation system comprising:
    a light; and
    a processor configured to:
        acquire, from a heart rate sensor, heart rate information related to a heart rate of a subject person;
        calculate a first heart rate variability from the heart rate information, a frequency band of the first heart rate variability being within a frequency band of a very low frequency component (VLF) of the heart rate information;
        calculate a second heart rate variability from the heart rate information, a frequency band of the second heart rate variability being (i) within the frequency band of the VLF of the heart rate information and (ii) lower than the frequency band of the first heart rate variability;
        estimate whether the subject person is in a concentration and effort state based on whether the second heart rate variability is equal to or lower than a predetermined level,
        generate a control signal, based on the first heart rate variability and the second heart rate variability, to increase concentration when the subject person is estimated to be in the concentration and effort state; and
        transmit the control signal to the light, the control signal being for controlling an adjustment of the light, wherein
    the light is configured to receive the control signal from the processor and, in response to receiving the control signal, adjust an illuminance of an environment of the subject person to influence a mental and physical condition of the subject person.

2. The mental and physical condition estimation system according to claim 1, the processor being further configured to:
    estimate whether the subject person is in a fatigue state based on whether the first heart rate variability is equal to or higher than a predetermined level, wherein
    the control signal is generated to alleviate fatigue when the subject person is estimated to be in the fatigue state.

3. The mental and physical condition estimation system according to claim 1, the processor being further configured to:
    set a target of a mental and physical condition of the subject person, wherein
    the control signal is further generated based on the target of the mental and physical condition.

4. The mental and physical condition estimation system according to claim 3, wherein the target of the mental and physical condition is set based on a predetermined schedule.

5. A mental and physical condition estimation method comprising:
    by a processor:
        acquiring, from a heart rate sensor, heart rate information related to a heart rate of a subject person;
        calculating a first heart rate variability from the heart rate information, a frequency band of the first heart rate variability being within a frequency band of a very low frequency component (VLF) of the heart rate information;
        calculating a second heart rate variability from the heart rate information, a frequency band of the second heart rate variability being (i) within the frequency band of the VLF of the heart rate information and (ii) lower than the frequency band of the first heart rate variability;
        estimating whether the subject person is in a concentration and effort state based on whether the second heart rate variability is equal to or lower than a predetermined level;
        generating a control signal, based on the first heart rate variability and the second heart rate variability, when the subject person is estimated to be in the concentration and effort state; and
        transmitting the control signal to a light, the control signal being for controlling an adjustment of the light, wherein
    the light is configured to receive the control signal from the processor and, in response to receiving the control signal, adjust an illuminance of an environment of the subject person to influence a mental and physical condition of the subject person.

6. A non-transitory storage medium that stores a mental and physical condition estimation program for causing a computer to execute:
    by a processor:
        acquiring, from a heart rate sensor, heart rate information related to a heart rate of a subject person;
        calculating a first heart rate variability from the heart rate information, a frequency band of the first heart rate variability being within a frequency band of a very low frequency component (VLF) of the heart rate information;
        calculating a second heart rate variability from the heart rate information, a frequency band of the second heart rate variability being (i) within the frequency band of the VLF of the heart rate information and (ii) lower than the frequency band of the first heart rate variability;
        estimating whether the subject person is in a concentration and effort state based on whether the second heart rate variability is equal to or lower than a predetermined level;
        generating a control signal, based on the first heart rate variability and the second heart rate variability, to increase concentration when the subject person is estimated to be in the concentration and effort state; and
        transmitting the control signal to a light, the control signal being for controlling an adjustment of the light, wherein the light is configured to receive the control signal from the processor and, in response to receiving the control signal, adjust an illuminance of an environment of the subject person to influence a mental and physical condition of the subject person.

* * * * *